(12) United States Patent
Cahoon et al.

(10) Patent No.: US 6,368,840 B1
(45) Date of Patent: Apr. 9, 2002

(54) ACYL-COA OXIDASE HOMOLOGUES

(75) Inventors: Edgar B. Cahoon; Rebecca E. Cahoon; William D. Hitz; Anthony J. Kinney, all of Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/342,647

(22) Filed: Jun. 29, 1999

Related U.S. Application Data

(60) Provisional application No. 60/092,482, filed on Jul. 10, 1998.

(51) Int. Cl.[7] .............................. C12N 9/02; C12N 1/21; C12N 5/04; C12N 1/19; C07N 21/04
(52) U.S. Cl. ................ 435/189; 435/252.3; 435/254.2; 435/320.1; 435/410; 536/23.2; 900/278; 900/295
(58) Field of Search .............................. 435/189, 252.3, 435/410.1, 254.2, 320.1; 536/23.2; 900/295, 278

(56) References Cited

U.S. PATENT DOCUMENTS

| | | |
|---|---|---|
| 5,994,622 A | 11/1999 | Jofuku et al. ............... 800/260 |
| 6,093,874 A | 7/2000 | Jofuku et al. ............... 800/260 |

OTHER PUBLICATIONS

Osumi T. et al. (1987) Biol. Chem. 262:8138–8143.
Picataggio, S. et al. (1991) Mol. Cell Biol. 11:4333–4339.
Bowman, J.L. et al. (1989) Plant Cell 1:37–52.
Leon–Kloosterziel, K. M. et al. (1994) Plant Cell 6:385–392.
Okamuro, J. et al. (1994) Proc. Natl. Acad. Sci. USA 94:7076–7081.
NCBI General Identifier No. 3044214.
NCBI General Identifier No. 3044212.
NCBI General Identifier No. 3115374.
NCBI General Identifier No. 2384696.
NCBI General Identifier No. 2370232.
NCBI General Identifier No. 1575556.
Plant Physiol. 112, 863 (1996).

*Primary Examiner*—Elizabeth Slobodyansky

(57) ABSTRACT

This invention relates to an isolated nucleic acid fragment encoding an acyl-CoA oxidase homologue. The invention also relates to the construction of a chimeric gene encoding all or a portion of the acyl-CoA oxidase homologue, in sense or antisense orientation, wherein expression of the chimeric gene results in production of altered levels of the acyl-CoA oxidase homologue in a transformed host cell.

13 Claims, 7 Drawing Sheets

```
SEQ ID NO:29       *
SEQ ID NO:26   MESRREKNPMTEEESDGLIAARRIQRLSLHLSPSLTLSPSLPLVQTETCSARSKKLDVNG
               PIPPNTTQKMQTPNCE---AERRIQRLTLHLNPT-ALVAAKQL-EMATC-ARGK-LSVDT  60
               1

SEQ ID NO:29   ** *** ******* ******* ** ***  *** ****** *** ** ******** **
SEQ ID NO:26   EALSLYMRGKHIDIQEKIFDFENSRPDLQTPIEISKDDHRELCMNQLIGLVREAGVRPFR
               PSLSSYMRGKHVDIQEKVFDYFNANPRLQTPVEISKDEHRDLCMXQLTGLVREAGIRPLR  120
               61

SEQ ID NO:29   ** *** ****** ****************** ***************************
SEQ ID NO:26   YVADDPEKYFAIMEAVGSVDMSLGIKMGVQYSLWGGSVINLGTKKHRDKYFDGIDNLDYT
               YVVDDPAKYFAILEAVGSVDMSLGIKMGVQYSLWGGSVLNLGTKKHKDKYFDGIDNLDYP  180
               121

SEQ ID NO:29   *** * ****** ***** ************** *** *********************
SEQ ID NO:26   GCFAMTELHHGSNVQGLQTTATFDPLKDEFVIDTPNDGAIKWWIGNAAVHGKFATVFARL
               GCFAMTELHHGSNVQGLQTVATFDIITDEFIINTPNDGAIKWWIGNAAVHGKFATVFARL  240
               181

SEQ ID NO:29   *** * ***** **  *** ************** *** *********************
SEQ ID NO:26   ILPTHDSKGVSDMGVHAFIVPIRDMKTHQTLPGVEIQDCGHKVGLNGVDNGALRFRSVRI
               KLPTYDKKGLSDMGVHAFIVPIRDMKTHQPLPGIEIHDCGHKVGLNGVDNGALRFRSVRI  300
               241

SEQ ID NO:29   **** * ********
SEQ ID NO:26   PRDNLLNRFGDVS
               PRDNXLNRFGDVS  312
               301
```

FIG. 1

```
SEQ ID NO:30   MEG-----IDHLADERNKAEFDVEDMKIVWAGSRHAFEVSDRIARLVASDPVFEKSNRAR
SEQ ID NO:02   M------AEVDHLAAERATARFDVEEMKVAWAGSRHAVHVADRMARLVASDPVFRKDNRTM
SEQ ID NO:04   ------------------------------------------------------------
SEQ ID NO:18   MEGGVGGEVDHLAGERATAQFDVEHMKVAWAGSRHAVDVADRMARLVASDPVFRKDNRTM
SEQ ID NO:28   MDAS--AEVDHLAAERSAARFDVEAMKVAWAGSRHAVEVGDRMARLVASDPVFRKDNRTM
                                                                           60
               1

SEQ ID NO:30   LSRKELFKSTLRKCAHAFKRIIELRLNEEEAGRLRHFIDQPAYVDLHWGMFVPAIKGQGT
SEQ ID NO:02   LSRKELFKDTLRKAAHAWKRIVELRLTEEEANLLRQYVDQPGYVDLHWGMFVPAIKGQGT
SEQ ID NO:04   ------------------------------------------------------------
SEQ ID NO:18   LPRKELFKDTLRKAAHAWKRIVELRLTEEEANLLRLYDQPGYVDLHWGMFVPAIKGQGT
SEQ ID NO:28   LSRKDLFKDTLRKAAHAWKRIVELRLTEEEAGMLRLYDQPGYVDLHWGMFVPAIKGQGT
                                                                          120
               61

*  ****
SEQ ID NO:30   EEQQKKWLSLANKMQIIGCYAQTELGHGSNVQGLETTATFDPKTDEFVIHTPTQTASKWW
SEQ ID NO:02   EEQQHKWLPLAYRFQIIGCYAQTELGHGSNVQGLETTATFDPKTDEFVIHSPTLTSSKWW
SEQ ID NO:04   ---------------------------------------------SARAQSLTSSKWW
SEQ ID NO:18   EEQQKKWLPLAYRFQIIGCYAQTELGHGSNVQGLETTATFDPKTDEFVIHSPTLTSSKWW
SEQ ID NO:28   EEQQKKWLPMAYKFQIIGCYAQTELGHGSNVQGLETTATFDPKTDEFVIHSPTLTSSKWW
                                                                          180
               121
```

FIG. 2A

```
SEQ ID NO:30        ************************************************************
SEQ ID NO:02  PGGLGKVSTHAVVYARLITNGKDYGIHGFIVQLRSLEDHSPLPNITVGDIGTKMGNGAYN
SEQ ID NO:04  PGGLGKASTHAVVYARLITEGKDYGIHGFIVQLRSLEDHSPLPGVTLGDIGGKFGSGAYN
SEQ ID NO:18  PGGLGKASTHAVVYARLITEGKDYGIHGFIVQLRSLEDHSPLPGVTLGDIGGKFGSGAYN
SEQ ID NO:28  PGGLGKASTHAVVYARLITEGKDYGIHGFIVQLRSLEDHSPLPGVTLGDIGGKFGSGAYN
              PGGLGKASTHAVVYARLITEGKDYGIHGFIVQLRSLEDHSPLPGVTLGDIGGKFGSGAYN
              181                                                          240

SEQ ID NO:30  *****  *  ************************  * **  *  *  ***  ********
SEQ ID NO:02  SMDNGFLMFDHVRIPRDQMLMRLSKVTREGEYVPSDVPKQLVYGTMVYVRQTIVADASNA
SEQ ID NO:04  SMDNGVLRFDHVRIPRDQMLMRLSQVTREGKYVHSNVPKQLLYGTMVYVRQSIVADASKA
SEQ ID NO:18  SMDNGVLRFDHVRIPRDQMLMRLSQVTREGKYVHSDVPKQLLYGTMVFVRQTIVADASKA
SEQ ID NO:28  SMDNGVLRFDHVRIPRDQMLMRLSQVTKEGKYVHSDVPKQLLYGTMVFVRQTIVADASKA
              SMDNGVLRFDHVRIPRDQMLMRLSQVTREGKYVHSDVPKQLLYGTMVFVRQTIVADASKA
              241                                                          300

SEQ ID NO:30  *****  **** *****  *  *       ***        **
SEQ ID NO:02  LSRAVCIATRYSAVRRQFGAHNGGIETQVIDYKTQQNRLFPLLASAYAFRFVGEWLKWLY
SEQ ID NO:04  LSRAVCIAVRYSAVRKQFGSQDGGPET---------QSRLFPLLASAYAFRFVGDWLKWLY
SEQ ID NO:18  LSRAVCIAVRYSAIRKQFGSQDGGPETKVLDYKTQQSRLFPLLASAYAFRFVGEWLKWLY
SEQ ID NO:28  LSRATCIAVRYSAIRKQFGPQTGGPETQVLNYKTQQSRLFPLLASAYAFRFVGEWLKWLY
              LSRAVCIAVRYSAIRKQFGSQDGGPETKVLDYKTQQSRLFPLLASAYAFRFVGDWLKWLY
              301                                                          360
```

FIG. 2B

```
                    *  *    **  ***********    **  *************   **  *************
SEQ ID NO:30   TDVTERLAASDFATLPEAHACTAGLKSLTTTATADGIEECRKLCGGHGYLWCSGLPELFA
SEQ ID NO:02   ---QKLEAKDFSTLQEAHACTAGLKAVTTSVTADAIEECRKLCGGHGYLNSSGLPELFA
SEQ ID NO:04   MDVTQKLEAKDYSTLQEAHACTAGLKAVTTSATADAIEECRKLCGGHGYLNSSGLPELFA
SEQ ID NO:18   TDVTHKLEAKDFSTLQEAHACTAGLKAVTTSATADGIEECRKLCGGHGYLNSSGLPELFA
SEQ ID NO:28   MDVTQKLEAKDYSTLQEAHACTAGLKAVTTSATADAIEECRKLCGGHGYLNSSGLPELFA
               361                                                         420

****************    **  *****    *****  *****     **    *****
SEQ ID NO:30   VYYPACTYEGDNVVLQLQVAREFLMKTVAQLGSGKVPVGTTAYMGRAAHLLQCRSGVQKAE
SEQ ID NO:02   VYYPACTYEGDNVVLLLQVARILMKTVSQLASGKQPVGTMAYMGKVQYLMQCKSAVSSAE
SEQ ID NO:04   VYYPACTYEGDNIVLLLQVARILMKTVSQLTSGKQPVGTMAYMGNVQYLMQCKCAVNTAE
SEQ ID NO:18   IYVPACTYEGDNVVLLLQVARILMKTVSQLASGKQPVGTMAYMGNIQYLMQCKCGVNTAE
SEQ ID NO:28   VYYPACTYEGDNIVLLLQVARILMKTVSQLTSGKQPVGTMAYMGNVQYLMQCKCAVNTAE
               421                                                         480

*****   *  **************    **    **    **    *  **  *********
SEQ ID NO:30   DWLNPDVVLEAFEARALRMAVTCAKNLSKFENQEQ--GFQELLADLVEAAIAHCQLIVVS
SEQ ID NO:02   DWLNPDAIQEAFEARALRMAVNCAQNISQAASQEEAAGFYERSPDLLEAAVAHIQLIIVT
SEQ ID NO:04   DWLNPVAIQEAFEARALRMAVNCAQNIGQAANQEE--GFYERSPDLLEAAVAHIQLVIVT
SEQ ID NO:18   DWLNPAAIREVEEARALRMAVNCAQNINKAPSQEE--GFYELSPDLLEVAVAHIQLIIVT
SEQ ID NO:28   DWLNPVAIQEAFEARALRMAVNCAQNIGQAANQEE--GFYERSPDLLEAAVAHIQLVIVT
               481                                                         540
```

FIG. 2C

```
SEQ ID NO:30    ****  *   *    *  ****    ****  **  **      **    *   *  **** *     *      *   ****  ***  *
SEQ ID NO:02    KFIAKLEQDIGGKGVKKQLNNLCYIYALYLLHKHLGDFLSTNCITPKQASLANDQLRSLY
SEQ ID NO:04    KFIEKVHQEIPGHGVKEQLQALCNVYALYILHKHLGDFLATGCITPRQGALANEQLSKLY
SEQ ID NO:18    KFIAKVQQDIPGPGVKEQLQNLCNVYALYILHKHLGDFLATGCITPKQGALANEQLGKLY
SEQ ID NO:28    KFIEKLEQDIPGEGVKEQLCILCNVYALYLVHKHLGDFLSTGSITARQGALANEQLGKLY
                KFIAKVQQDIPGPGVKEQLQNLCNVYALYILHKHLGDFLATGCITPKQGALANEQLGKLY
                541                                                        600

SEQ ID NO:30     ***  ***************  ***    *** ***  ***   *  ** **  ****
SEQ ID NO:02    TQVRPNAVALVDAFNYTDHYLNSVLGRYDGNVYPKLFEEALKDPLNDSVVPDGYQEYLRP
SEQ ID NO:04    AQVRPNAVALVDAFNYTDHYLGSVLGRYDGDVYPALYEEAWKDPLNETVVPEGYHEYLRP
SEQ ID NO:18    AQVRPNAVALVDAFNYTDHYLGSVLGRYDGNVYPALYEEAWKDPLNETVVPEGYHEYLRP
SEQ ID NO:28    AQVRPNAVALVDAFNYTDHYLGSVLGRYDGNVYPALYEEAWKDPLNDTDVPDGYQEHLRP
                AQVRPNAVALVDAFNYTDHYLGSVLGRYDGNVYPALYEEAWKDPLNETVVPEGYHEYLRP
                601                                                        660

SEQ ID NO:30     **  * *******
SEQ ID NO:02    VL-QQQLRTARL
SEQ ID NO:04    LIKQQQLKLSRL
SEQ ID NO:18    LLKQQ-LKLSRL
SEQ ID NO:28    LLKQQ-LKLSRL
                LLKQQ-LKLSRL
                661       673
```

FIG. 2D

```
                            *        ****      **    * ****  * *   ** *   * *******
SEQ ID NO:31   ------------LEVGGRVLGVHALLVPLRDPAGKVLPGIRIEDCGEKMGLNGVDN
SEQ ID NO:10   GPEFPGRPTRPIVFCQLHINGRNEGVHAFVAQIRDEDGTVLPNIHIADCGHKIGLNGVDN  60
               1

******  * **********  *    *  **   *  *  ***    *        *
SEQ ID NO:31   GRIWFEHVRVRPRENLLDREGQVNAQGEYTSAITGDSKRFFTMLGTLVAGRVSVAAAALSA
SEQ ID NO:10   GRIWFQNIRVPRENLLNLVADVLPDGRYVSMIDNPDQRFAAFLSPLTLGRVNIAVNSVYI  120
               61

*  *****  *  *  *            **   *******   **  * *****   *
SEQ ID NO:31   AKSGLTIAVRYGDLRRQFGPAGDK-EFRLLDHQAHQRRLLVPLAKTYAMDFALEYLVERY
SEQ ID NO:10   SKVSLAIAVRYSLSRRAFSIAPDAPEMLLLDYPSHQRRLLPLLAKVCLMSSAGNFMKNMY  180
               121

*****  *      *** **  *  **  ******  ** *********         **
SEQ ID NO:31   VKRTEEDAREVESLAAGLKAYSTWHTTAVLQEAREACGGQYLQANRLAALKADTDVFTT
SEQ ID NO:10   VKRTPEMSKDIHIYSSALKATLTWQNMITIQECREACGGQGLKTENRIGIFKSEFDVQST  240
               181

*****  ***   *       *  *           *         *         **
SEQ ID NO:31   FEGDNTVLMQLVAKGLLTGYRQRFEDDRVFAVLKLLADRATAVVDRNPFAARRTDSDHLR
SEQ ID NO:10   FEGDNNVLMQQVSKALYAEFLGAQKKQQPFKGLGL-----EHLNGSSPVIPDKLTSSILR  300
               241
```

FIG. 3A

```
                        **  *                    *    **    *  **  *
SEQ ID NO:31   DNDYHLRALRFREEELLATVSQRIRKRLSAGVEAFEAFNQVQVHLLELAHAHVERLVLEQ
SEQ ID NO:10   SSKFQMDLFCLRERDLLKQFVEEVSLHLAQGESREKALMLSYQVAEDLARAFTERTILQI
               301                                                         360

**      *  ****  *         *     *         *   ****  **    *
SEQ ID NO:31   FLKGVADVKDPGLKTVLGRLCDLYGLSCLESANGWFQEHGWLEGTKVKAIRKEVTRLCAE
SEQ ID NO:10   FLEDEMNVPSGSLKEVLGLLRSLYVMVNIDESTS-FLRYGHLSRDNVALVRKEVLKLCSE
               361                                                         420

***  *   *  ***  *   *
SEQ ID NO:31   LRPDAVALVNAFGVPDTCLAAPIGLGHLS-------P
SEQ ID NO:10   LRPHALAVVSSFGIPDAFLS-PLAEDWIEANALSTGSH
               421                                 459
```

FIG. 3B

ACYL-CoA OXIDASE HOMOLOGUES

This application claims the benefit of U.S. Provisional Application No. 60/092,482, filed Jul. 10, 1998.

FIELD OF THE INVENTION

This invention is in the field of plant molecular biology. More specifically, this invention pertains to nucleic acid fragments encoding acyl-CoA oxidase homologues in plants and seeds.

BACKGROUND OF THE INVENTION

The first step in the beta-oxidation pathway is catalyzed by acyl-CoA oxidase, an oxidoreductase which requires FAD as a cofactor. Acyl-CoA oxidase acts on the CH—CH group of donors using oxygen as an acceptor molecule. It catalyzes the following reaction:

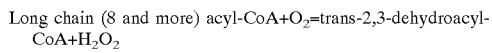

Long chain (8 and more) acyl-CoA+$O_2$=trans-2,3-dehydroacyl-CoA+$H_2O_2$

Acyl-CoA oxidase (EC 1.3.3.6) has been widely studied in human tissues where it has been found localized in the peroxisomes. Acyl-CoA oxidase genes have also been described in other mammals, as well as in bacteria and yeast. The gene encoding a putative acyl-CoA oxidase from *Hordeum vulgare* has been isolated and expressed in vitro. Genomic sequencing projects have found homologous genes in *Arabidopsis thaliana*, Phalaenopsis sp. and *Oryza sativa*. Studies on the rat acyl-CoA oxidase gene indicate that two species of mRNA are produced by possible alternative splicing; Southern blots indicate a single copy gene (Osumi T., et al. (1987) *Biol Chem* 262:8138–8143). The two forms of the enzyme (acyl-CoA oxidase 1 and 2) differ only within a small region of about 30 amino acids, and contain the same number of amino acids. In the yeast *Candida tropicalis*, isozymes of acyl-CoA have been described (Picataggio, S. et al. (1991) *Mol. Cell. Biol.* 11:4333–4339). Gene disruptions revealed the diploid nature of this alkane- and fatty acid-utilizing yeast by showing that it contains two copies of each gene. The two isozymes are differentially regulated and display unique substrate profiles and kinetic properties.

The instant cDNAs for acyl-CoA oxidase also show homology to an *Arabidopsis thaliana* chromosome 4 homologue of the TINY region of the Arabidopsis apetela2 gene (AP2) from amino acids 234–885 of the 895 amino acid sequence. Apetela2 is a homeotic gene involved in setting up or responding to concentric or overlapping fields within the flower primordium (Bowman, J. L. et al. (1989) *Plant Cell* 1:37–52). An apetela2 mutation (ap2-1) has a pleitotropic effect on seeds: *Arabidopsis thaliana* ap2-1 seed shape will vary from the normal oblong shape to a variety of aberrant shapes (Leon-Kloosterziel, K. M. et al. (1994) *Plant Cell* 6:385–392). The AP2 domain has been linked to increased seed size and protein content in seeds (Okamuro, J. et al., (1994) *Proc. Natl. Acad. Sci. USA* 94:7076–7081).

Accordingly, acyl-CoA oxidase is a key step in beta-oxidation of fatty acids in plants. Manipulation of this step in the breakdown of fatty acids may allow transgenic plants to accumulate significant amounts of unusual fatty acids in their seed. This would facilitate the development of transgenic plants that produce novel oils.

SUMMARY OF THE INVENTION

The instant invention relates to isolated nucleic acid fragments encoding acyl-CoA oxidase homologues. Specifically, this invention concerns an isolated nucleic acid fragment encoding an acyl-CoA oxidase homologue and an isolated nucleic acid fragment that is substantially similar to an isolated nucleic acid fragment encoding an acyl-CoA oxidase homologue. In addition, this invention relates to a nucleic acid fragment that is complementary to the nucleic acid fragment encoding acyl-CoA oxidase homologue.

An additional embodiment of the instant invention pertains to a polypeptide encoding all or a substantial portion of an acyl-CoA oxidase homologue.

In another embodiment, the instant invention relates to a chimeric gene encoding an acyl-CoA oxidase homologue, or to a chimeric gene that comprises a nucleic acid fragment that is complementary to a nucleic acid fragment encoding an acyl-CoA oxidase homologue, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding an acyl-CoA oxidase homologue, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of an acyl-CoA oxidase homologue in a transformed host cell comprising: a) transforming a host cell with a chimeric gene comprising a nucleic acid fragment encoding an acyl-CoA oxidase homologue; and b) growing the transformed host cell under conditions that are suitable for expression of the chimeric gene wherein expression of the chimeric gene results in production of altered levels of acyl-CoA oxidase homologue in the transformed host cell.

An addition embodiment of the instant invention concerns a method for obtaining a nucleic acid fragment encoding all or a substantial portion of an amino acid sequence encoding an acyl-CoA oxidase homologue.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIG. 1 depicts the alignment between the acyl-CoA oxidase amino acids 1 through 312 from *Arabidopsis thaliana* (NCBI General Identifier No. 3044212; SEQ ID NO:29) and the instant soybean containing assembled from clones sf11.pk126.i21, sf11.pk130.l22, sgc6c.pk001.c23 and src2c.pk024.a19 (SEQ ID NO:26). The top row indicates with asterisks (*) the amino acids conserved in both sequences.

FIG. 2 depicts the amino acid sequence alignment between the acyl-CoA oxidase from *Arabidopsis thaliana* (NCBI General Identifier No. 3044214; SEQ ID NO:30), the instant corn clone cc2.pk0012.h1 (SEQ ID NO:2), the instant corn clone chpc24.pk0002.e1 (SEQ ID NO:4), the instant rice clone rls6.pk0014.c9 (SEQ ID NO:18) and the instant wheat clone w11n.pk0102.e8 (SEQ ID NO:28). The top row indicates with asterisks (*) the amino acids conserved among all sequences.

FIG. 3 depicts the amino acid sequence alignment between the acyl-CoA oxidase from *Myxococcus xanthus* (NCBI General Identifier No. 2384696; SEQ ID NO:31), the instant corn contig assembled from clones cbn10.pk0031.h10, p0010.cbpbk39rb and p0090.cspsp39rb (SEQ ID NO:10). The top row indicates with asterisks (*) the amino acids conserved among both sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Acyl-CoA Oxidase Homologues

| | | SEQ ID NO: | |
|---|---|---|---|
| Protein | Clone Designation | (Nucleotide) | (Amino Acid) |
| Corn Acyl-CoA Oxidase | cc2.pk0012.h1 | 1 | 2 |
| Corn Acyl-CoA Oxidase | chpc24.pk0002.e1 | 3 | 4 |
| Corn Acyl-CoA Oxidase | p0005.cbmex03r | 5 | 6 |
| Corn Acyl-CoA Oxidase | p0057.cvrai89r | 7 | 8 |
| Corn Acyl-CoA Oxidase | Contig of:<br>cbn10.pk0031.h10<br>p0010.cbpbk39rb<br>p0090.cspsp39rb | 9 | 10 |
| Prickly Poppy Acyl-CoA Oxidase | pps1c.pk004.19 | 11 | 12 |
| Rice Acyl-CoA Oxidase | r10n.pk122.b9 | 13 | 14 |
| Rice Acyl-CoA Oxidase | r1r6.pk0052.e11 | 15 | 16 |
| Rice Acyl-COA Oxidase | r1s6.pk0014.c9 | 17 | 18 |
| Soybean Acyl-CoA Oxidase | Contig of:<br>sfl1.pk0066.g9-3'<br>sdp4c.pk027.g10 | 19 | 20 |
| Soybean Acyl-CoA Oxidase | ses9c.pk003.g17 | 21 | 22 |
| Soybean Acyl-CoA Oxidase | Contig of:<br>sfl1.pk0066.g9-5'<br>sre.pk0001.e12 | 23 | 24 |
| Soybean Acyl-CoA Oxidase | Contig of:<br>sfl1.pk126.i21<br>sfl1.pk130.122<br>sgc6c.pk001.c23<br>src2c.pk024.a19 | 25 | 26 |
| Wheat Acyl-CoA Oxidase | w11n.pk0102.e8 | 27 | 28 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent similarity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% similar to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent similarity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol*. 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacteriun-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several acyl-CoA oxidase homologues have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other acyl-CoA oxidase homologues, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673; Loh et al. (1989) *Science* 243:217). Products generated by the 3' and 5' RACE procedures can be combined to generate full-length cDNAs (Frohman and Martin (1989) *BioTechniques* 1: 165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of oxidized long-chain Acyl-CoA and thus the oil content in those cells. Suppression of this gene may lead to increased oil content or suitable genetic background for expression of novel desaturase-related enzymes. Prickly poppy makes unusual fatty acids, expression of the prickly poppy acyl-CoA oxidase in other crops may allow the accumulation of novel fatty acids.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense synthase enzyme genes may require the use of different chimeric genes utilizing different regulatory elements known to the skilled artisan. Once transgenic plants are obtained by one of the methods described above, it will be necessary to screen individual transgenics for those that most effectively display the desired phenotype. It is well known to those skilled in the art that individual transgenic plants carrying the same construct may differ in expression levels; this phenomenon is commonly referred to as "position effect". For example, when the construct in question is designed to express higher levels of the gene of interest, individual plants will vary in the amount of the protein produced and thus in enzyme activity; this in turn will effect the phenotype. Thus, in the use of these techniques their efficiency in an individual transgenic plant is unpredictable, but given a large transgenic population individuals with suppressed gene expression will be obtained. In either case, in order to save time, the person skilled in the art will make multiple genetic constructs containing one or more different parts of the gene to be suppressed, since the art does not teach a method to predict which will be most effective for a particular gene. Furthermore, even the most effective constructs will give an effective suppression phenotype only in a fraction of the individual transgenic lines isolated. For example, WO 93/11245 and WO 94/11516 disclose that when attempting to suppress the expression of fatty acid desaturase genes in canola, actual suppression was obtained in less than 1% of the lines tested. In other species the percentage is somewhat higher, but in no case does the percentage reach 100. This should not be seen as a limitation on the present invention, but instead as practical matter that is appreciated and anticipated by the person skilled in this art. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that the majority of samples will be negative.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded acyl-CoA oxidase homologue. An example of a vector for high level expression of the instant polypeptides in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4(1).37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet*. 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res*. 18:3671), Radiation Hybrid Mapping (Walter et al. (1997) *Nature Genetics* 7:22–28) and Happy Mapping (Dear and Cook (1989) *Nucleic Acid Res*. 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402; Koes et al. (1995) *Proc. Natl. Acad. Sci USA* 92:8149; Bensen et al. (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1
Composition of cDNA Libraries, Isolation and Sequencing of cDNA Clones cDNA libraries representing mRNAs from various corn, prickly poppy, rice, soybean and wheat tissues were prepared. The characteristics of the libraries are described below.

TABLE 2 cDNA Libraries from Corn, Prickly Poppy, Rice, Soybean and Wheat

| Library | Tissue | Clone |
| --- | --- | --- |
| cbn10 | Corn Developing Kernel (Embryo and Endosperm); 10 Days After Pollination | cbn10.pk0031.h10 |
| cc2 | Corn Callus, Partially Differentiated | cc2.pk0012.h1 |
| chpc24 | Corn (MBS847) 8 Day Old Shoot Treated 24 Hours With Herbicide* | chpc24.pk0002.e1 |
| p0005 | Corn Immature Ear | p0005.cbmex03r |
| p0010 | Corn Log Phase Suspension Cells Treated With A23187** to Induce Mass Apoptosis | p0010.cbpbk39rb |
| p0057 | Corn Root Seedlings Radicle and Lateral Seminal Roots, Growth Stage V1*** With Two Visible Leaves | p0057.cvrai89r |
| p0090 | Corn Seedlings After 10 Day Drought Stress, Heat Shocked for 8, 16, 24 hours at 45° C. RNA prepared for each time point and pooled.**** | p0090.cspsp39rb |
| pps1c | Prickly Poppy Developing Seeds | pps1c.pk004.l9 |
| rl0n | Rice 15 Day Old Leaf**** | rl0n.pk122.b9 |
| rlr6 | Rice Leaf 15 Days After Germination, 6 Hours After Infection of Strain *Magaporthe grisea* 4360-R-62 (AVR2-YAMO); Resistant | rlr6.pk0052.e11 |
| rls6 | Rice Leaf 15 Days After Germination, 6 Hours After Infection of Strain *Magaporthe grisea* 4360-R-67 (AVR2-YAMO); Susceptible | rls6.pk0014.c9 |
| sdp4c | Soybean Developing Pods (10–12 mm) | sdp4c.pk027.g10 |
| ses9c | Soybean Embryogenic Suspension | ses9c.pk003.g17 |
| sfl1 | Soybean Immature Flower | sfl1.pk0066.g9 sfl1.pk126.i21 sfl1.pk130.l22 |
| sgc6c | Soybean Cotyledon 16–26 Days After Germination (all yellow) | sgc6c.pk001.c23 |
| src2c | Soybean 8 Day Old Root Infected With Cyst Nematode | src2c.pk024.a19 |
| sre | Soybean Root Elongation Zone 4 to 5 Days After Germination | sre.pk0001.e12 |
| wl1n | Wheat Leaf From 7 Day Old Seedling**** | wl1n.pk0102.e8 |

*Application of 2-[(2,4-dihydro-2,6,9-trimethyl[1]benzothiopyrano[4,3-c]pyrazol-8-yl)carbonyl]-1,3-cyclohexanedione S,S-dioxide; synthesis and methods of using this compound are described in WO 97/19087, incorporated herein by reference.
**A23187 is commercially available from several vendors including Calbiochem.
***Corn developmental stages are explained in the publication "How a corn plant develops" from the Iowa State University Coop. Ext. Service Special Report No. 48 reprinted June 1993.
****These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP* XR vectors according to the manufacturer's protocol (Stratagene Cloning Systems, La Jolla, Calif.). The Uni-ZAP* XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer.

Example 2
Identification of cDNA Clones cDNA clones encoding acyl-CoA oxidase homologues were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3
Characterization of cDNA Clones Encoding Acyl-CoA Oxidase Homologues

The BLASTX search using the nucleotide sequences from clones listed in Table 3 revealed similarity of the polypeptides encoded by the cDNAs to acyl-CoA oxidase from *Arabidopsis thaliana* (NCBI General Identifier No. 3044214 or 3044212), Cucurhita sp (NCBI General Identifier No. 3115374), *Myxococcus xanthus* (NCBI General Identifier No. 2384696) and Phalaenopsis sp. True Lady (NCBI General Identifier No. 1575556). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to Acyl-CoA Oxidase Homologues

| Clone | Status | NCBI General Identifier No. | BLAST pLog Score |
|---|---|---|---|
| cc2.pk0012.h1 | FIS | 3044214 | 254.00 |
| chpc24.pk0002.e1 | FIS | 3044214 | 254.00 |
| p0005.cbmex03r | EST | 3115374 | 30.00 |
| p0057.cvrai89r | EST | 1575556 | 58.70 |
| Contig of:<br>cbn10.pk0031.h10<br>p0010.cbpbk39rb<br>p0090.cspsp39rb | Contig | 2384696 | 76.40 |
| pps1c.pk004.19 | EST | 3044214 | 46.22 |
| r10n.pk122.b9 | EST | 1575556 | 60.10 |
| r1r6.pk0052.e11 | EST | 1575556 | 66.70 |
| r1s6.pk0014.c9 | FIS | 3044214 | 254.00 |
| Contig of:<br>sdp4c.pk027.g10<br>sfl1.pk0066.g9-3' | Contig | 2384696 | 9.70 |
| ses9c.pk003.g17 | EST | 3044214 | 32.00 |
| Contig of:<br>sfl1.pk0066.g9-5'<br>sre.pk0001.e12 | Contig | 3115374 | 30.52 |
| Contig of:<br>sfl1.pk126.i21<br>sfl1.pk130.l22<br>sgc6c.pk001.c23<br>src2c.pk024.a19 | Contig | 3044212 | 150.00 |
| wl1n.pk0102.e8 | FIS | 3044214 | 254.00 |

FIG. 1 presents an alignment of the amino acid sequences set forth in SEQ ID NO:26 and amino acids 1 through 312 from the *Arabidopsis thaliana* acyl-CoA oxidase homologue sequence (NCBI General Identifier No. 3044212; SEQ ID NO:29). FIG. 3 presents an alignment of the amino acid sequences set forth in SEQ ID NO:10 and the *Myxococcus xanthus* acyl-CoA oxidase homologue sequence (SEQ ID NO:31). FIG. 2 presents an alignment of the amino acid sequences set forth in SEQ ID NOS:2, 4, 18 and 28 and the *Arabidopsis thaliana* acyl-CoA oxidase homologue sequence (NCBI General Identifier No. 3044214; SEQ ID NO:30). The data in Table 4 represents a calculation of the percent identity of the amino acid sequences set forth in SEQ ID NOs:2, 4, 6, 8, 10, 12, 14, 16, 18, 20, 22, 24, 26 and 28 and the acyl-CoA oxidase homologue from *Arabidopsis thaliana* (NCBI General Identifier No. 3044214 or 3044212), Cucurbita sp (NCBI General Identifier No. 3115374), *Myxococcus xanthus* (NCBI General Identifier No. 2384696) or Phalaenopsis sp. True Lady (NCBI General Identifier No. 1575556).

TABLE 4

Percent Identity of Amino Acid Sequences Deduced From the Nucleotide Sequences of cDNA Clones Encoding Polypeptides Homologous to Acyl-CoA Oxidase

| SEQ ID NO. | Percent Identity | NCBI General Identifier No. |
|---|---|---|
| 2 | 75.6 | 3044214 |
| 4 | 76.3 | 3044214 |
| 6 | 42.8 | 3115374 |
| 8 | 84.6 | 1575556 |
| 10 | 37.4 | 2384696 |
| 12 | 68.6 | 3044214 |
| 14 | 70.6 | 1575556 |
| 16 | 83.3 | 1575556 |
| 18 | 78.3 | 3044214 |
| 20 | 34.8 | 2384696 |
| 22 | 55.8 | 3044214 |
| 24 | 43.3 | 3115374 |
| 26 | 75.5 | 3044212 |
| 28 | 78.0 | 3044214 |

The deduced acid sequence sequences from clones cc2.pk0012.h1 (SEQ ID NO:2) and chpc24.pk0002.e1 (SEQ ID NO:4) are 84.5% identical. The amino acid sequence from SEQ ID NO:2 has a 37 amino acid deletion compared to SEQ ID NO:4 and to SEQ ID NO:30. This deletion corresponds to amino acids 322 through 359 of the *Arabidopsis thaliana* sequence and appears to be the result of a differential splicing event.

Sequence alignments and percent similarity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode two portions (13 and 20%) and three entire corn acyl-CoA oxidase homologues, a portion of prickly poppy (20%) acyl-CoA oxidase homologue, two portions (20%) and an entire rice acyl-CoA oxidase homologues, four portions of soybean acyl-CoA oxidase homologues, and one entire wheat acyl-CoA oxidase homologue. These sequences represent unique corn, prickly poppy, rice, soybean and wheat sequences encoding acyl-CoA oxidase homologues.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15°

C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5
Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba 1. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl₂ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6
Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having acyl CoA oxidase activity, wherein the amino acid sequence of the polypeptide and the amino acid sequence of SEQ ID NO:2, SEQ ID NO:18, or SEQ ID NO:28 have at least 90% sequence identity, or
   (b) the complement of the nucleotide sequence, wherein the complement and the nucleotide sequence contain the same number of nucleotides and are 100% complementary.

2. The polynucleotide of claim 1, wherein the amino acid sequence of the polypeptide and the amino acid sequence of SEQ ID No:2, SEQ ID NO:18, or SEQ ID NO:28 have at least 95% sequence identity.

3. The polynucleotide of claim 1, wherein the nucleotide sequence comprises the nucleotide sequence of SEQ ID NO:1, SEQ ID NO:17, or SEQ ID NO:27.

4. The polynucleotide of claim 1, wherein the polypeptide comprises the amino acid sequence of SEQ ID NO:2, SEQ ID NO:18, or SEQ ID NO:28.

5. A vector comprising the polynucleotide of claim 1.

6. A chimeric gene comprising the polynucleotide of claim 1 operably linked to a regulatory sequence.

7. A method for transforming a cell comprising transforming a cell with the polynucleotide of claim 1.

8. A cell comprising the chimeric gene of claim 6.

9. The cell of claim 8, wherein the cell is a yeast cell, a bacteria cell, or a plant cell.

10. A method for producing a plant comprising transforming a plant cell with the polynucleotide of claim 1 and regenerating a plant from the transformed plant cell.

11. A plant comprising the chimeric gene of claim 6.

12. A seed comprising the chimeric gene of claim 6.

13. A method for altering the level of acyl-CoA oxidase expression in a host cell comprising:
 (a) transforming a host cell with the chimeric gene of claim 6, and
 (b) growing the cell transformed in (a) under conditions suitable for the expression of the chimeric gene.

* * * * *

SEQUENCE LISTING

```
<160> NUMBER OF SEQ ID NOS: 31

<210> SEQ ID NO 1
<211> LENGTH: 2230
<212> TYPE: DNA
<213> ORGANISM: Zea mays

<400> SEQUENCE: 1
gcacgaggcg gaagccagca cctcaaagcc atggcggaag tggaccacct cgctgccgag      60
agggccaccg cgcgcttcga cgtcgaggag atgaaggttg cgtgggccgg ctcacgccac     120
gccgtccacg tcgccgaccg catggcgcgc ctcgtcgcat ccgaccctgt cttccgcaag     180
```

-continued

```
gataacagga ccatgctctc caggaaggag ttgttcaagg acactctaag aaaagcagcg    240
catgcgtgga agcggattgt cgagctacgt cttacagaag aggaagcgaa tttgctgaga    300
caatatgttg accagcctgg ttatgttgat ctgcattggg catgttcgt tccagctata     360 aaaggccaag gaactgagga gcagcagcac aagtggttac cactggctta caagttccaa    420
ataattgggt gctatgctca gacggaactt ggtcatggct caaacgttca gggccttgaa    480
acaactgcta cattcgatcc aaagactgat gagtttgtca tccacagtcc aactctcacg    540
tccagcaaat ggtggcctgg tggcttgggg aaagcttcca cccatgcagt ggtgtacgct    600
cggttgataa ctgaaggaaa ggactatggc atacatggtt tcattgtgca actgcgaagc    660
ttagaggatc actccccact tcctggtgtt accctcggtg atattggtgg aaagttcggt    720
agtggtgcat ataacagtat ggataatggt gttcttcgat ttgaccatgt gcgcatccca    780
agggatcaaa tgttgatgag ctttcacaa gttacaaggg aggggaaata tgttcactca     840
aatgttccaa gcagctgct gtatgggaca atggtttacg ttcgccagtc aattgttgca     900
gatgcttcta aggctttgtc ccgtgctgtt tgcattgctg tacgatacag cgcagtccga    960
aagcagtttg gctctcaaga tggtggccct gagactcaga aactggaagc caaggacttc   1020
tcgacgctgc aggaagctca tgcatgcact gctggtttga agctgtgac aacatcagta    1080 acagctgatg caattgaaga atgccgaaag ctctgtggtg acatggtta cttgaacagc    1140 agtgggcttc ctgagttgtt tgcggtctat gttcccgctt gcacttacga aggagacaac   1200
gtcgttttgc ttttgcaggt tgcaaggatt ctaatgaaaa ccgtttctca gttggcatcc   1260
gggaaacagc ctgttggcac aatggcctac atgggcaaag tgcagtattt gatgcaatgc   1320
aaatctgctg tcagttcagc tgaagattgg cttaaccctg atgccataca agaggcattt   1380
gaagcaagag cgctcagaat ggcggtaaac tgtgcccaga acataagcca agctgcaagc   1440
caagaggaag ctgcaggttt ctatgagcgg tcccccagatt tgcttgaggc tgcggtagct   1500
cacatccagc tgattatcgt gaccaagttt attgagaagg tgcatcagga gattcctgga   1560
cacggagtga aggaacagct ccaggccctc tgcaacgtgt acgcgctgta catcctccac   1620
aagcacctgg gcgacttctt ggcgactggg tgcatcacgc ccaggcaggg agcgctggca   1680
aacgagcagc tgagcaagct gtacgcgcag gtgcgtccga acgctgtggc gctggtggat   1740
gcgttcaact acacggacca ctacctgggg tctgtgctgg ggcggtacga cggcgacgtg   1800
taccctgcgc tctacgagga ggcgtggaag gacccgctga cgagacggt ggtgccggag    1860 gggtatcacg agtacctccg cccactcatc aagcagcagc agctcaagct ctcgaggctc   1920
tgaatcctct ctctctctct ctctctctct ctctctctga tgtggaagcc agccaagatg   1980
tgtgtacgtt agacatgtgt ggtgggttcg ttgatacacg agggagtgag taataaagag   2040
cgaacgagag atggaacaaa gaactgaatt tgtatcgtac agcaaagaac ttaatttgct   2100
gttactgacc acgtgattgg ttgttaggat cagcagatcc tggtcgaagc ctatatgcag   2160
gctgggctta gcctgtatgc attgatgcaa actaaaataa attctttttt aaaaaaaaaa   2220
aaaaaaaaa                                                           2230
```

<210> SEQ ID NO 2
<211> LENGTH: 630
<212> TYPE: PRT
<213> ORGANISM: Zea mays

<400> SEQUENCE: 2

Met Ala Glu Val Asp His Leu Ala Ala Glu Arg Ala Thr Ala Arg Phe

```
  1               5                   10                  15
Asp Val Glu Glu Met Lys Val Ala Trp Ala Gly Ser Arg His Ala Val
                     20                  25                  30
His Val Ala Asp Arg Met Ala Arg Leu Val Ala Ser Asp Pro Val Phe
             35                  40                  45
Arg Lys Asp Asn Arg Thr Met Leu Ser Arg Lys Glu Leu Phe Lys Asp
         50                  55                  60
Thr Leu Arg Lys Ala Ala His Ala Trp Lys Arg Ile Val Glu Leu Arg
 65                  70                  75                  80
Leu Thr Glu Glu Glu Ala Asn Leu Leu Arg Gln Tyr Val Asp Gln Pro
                 85                  90                  95
Gly Tyr Val Asp Leu His Trp Gly Met Phe Val Pro Ala Ile Lys Gly
             100                 105                 110
Gln Gly Thr Glu Glu Gln Gln His Lys Trp Leu Pro Leu Ala Tyr Lys
         115                 120                 125
Phe Gln Ile Ile Gly Cys Tyr Ala Gln Thr Glu Leu Gly His Gly Ser
     130                 135                 140
Asn Val Gln Gly Leu Glu Thr Thr Ala Thr Phe Asp Pro Lys Thr Asp
145                 150                 155                 160
Glu Phe Val Ile His Ser Pro Thr Leu Thr Ser Ser Lys Trp Trp Pro
             165                 170                 175
Gly Gly Leu Gly Lys Ala Ser Thr His Ala Val Val Tyr Ala Arg Leu
         180                 185                 190
Ile Thr Glu Gly Lys Asp Tyr Gly Ile His Gly Phe Ile Val Gln Leu
     195                 200                 205
Arg Ser Leu Glu Asp His Ser Pro Leu Pro Gly Val Thr Leu Gly Asp
210                 215                 220
Ile Gly Lys Phe Gly Ser Gly Ala Tyr Asn Ser Met Asp Asn Gly
225                 230                 235                 240
Val Leu Arg Phe Asp His Val Arg Ile Pro Arg Asp Gln Met Leu Met
             245                 250                 255
Arg Leu Ser Gln Val Thr Arg Glu Gly Lys Tyr Val His Ser Asn Val
         260                 265                 270
Pro Lys Gln Leu Leu Tyr Gly Thr Met Val Tyr Val Arg Gln Ser Ile
     275                 280                 285
Val Ala Asp Ala Ser Lys Ala Leu Ser Arg Ala Val Cys Ile Ala Val
     290                 295                 300
Arg Tyr Ser Ala Val Arg Lys Gln Phe Gly Ser Gln Asp Gly Gly Pro
305                 310                 315                 320
Glu Thr Gln Lys Leu Glu Ala Lys Asp Phe Ser Thr Leu Gln Glu Ala
             325                 330                 335
His Ala Cys Thr Ala Gly Leu Lys Ala Val Thr Thr Ser Val Thr Ala
         340                 345                 350
Asp Ala Ile Glu Glu Cys Arg Lys Leu Cys Gly Gly His Gly Tyr Leu
     355                 360                 365
Asn Ser Ser Gly Leu Pro Glu Leu Phe Ala Val Tyr Val Pro Ala Cys
370                 375                 380
Thr Tyr Glu Gly Asp Asn Val Val Leu Leu Gln Val Ala Arg Ile
385                 390                 395                 400
Leu Met Lys Thr Val Ser Gln Leu Ala Ser Gly Lys Gln Pro Val Gly
             405                 410                 415
Thr Met Ala Tyr Met Gly Lys Val Gln Tyr Leu Met Gln Cys Lys Ser
         420                 425                 430
```

```
Ala Val Ser Ser Ala Glu Asp Trp Leu Asn Pro Asp Ala Ile Gln Glu
            435                 440                 445

Ala Phe Glu Ala Arg Ala Leu Arg Met Ala Val Asn Cys Ala Gln Asn
        450                 455                 460

Ile Ser Gln Ala Ala Ser Gln Glu Glu Ala Ala Gly Phe Tyr Glu Arg
465                 470                 475                 480

Ser Pro Asp Leu Leu Glu Ala Ala Val Ala His Ile Gln Leu Ile Ile
                485                 490                 495

Val Thr Lys Phe Ile Glu Lys Val His Gln Glu Ile Pro Gly His Gly
            500                 505                 510

Val Lys Glu Gln Leu Gln Ala Leu Cys Asn Val Tyr Ala Leu Tyr Ile
        515                 520                 525

Leu His Lys His Leu Gly Asp Phe Leu Ala Thr Gly Cys Ile Thr Pro
    530                 535                 540

Arg Gln Gly Ala Leu Ala Asn Glu Gln Leu Ser Lys Leu Tyr Ala Gln
545                 550                 555                 560

Val Arg Pro Asn Ala Val Ala Leu Val Asp Ala Phe Asn Tyr Thr Asp
                565                 570                 575

His Tyr Leu Gly Ser Val Leu Gly Arg Tyr Asp Gly Asp Val Tyr Pro
            580                 585                 590

Ala Leu Tyr Glu Glu Ala Trp Lys Asp Pro Leu Asn Glu Thr Val Val
        595                 600                 605

Pro Glu Gly Tyr His Glu Tyr Leu Arg Pro Leu Ile Lys Gln Gln Gln
    610                 615                 620

Leu Lys Leu Ser Arg Leu
625                 630

<210> SEQ ID NO 3
<211> LENGTH: 1794
<212> TYPE: DNA
<213> ORGANISM: Zea mays

<400> SEQUENCE: 3
ttcggcacga gcgcagtctc tgacctccag caaatggtgg cctggtggct tggggaaagc      60
ttccactcat gcagtggtgt atgctcggct gataactgaa ggaaaggact atggtataca     120
tggtttcatt gtgcaactgc gaagcttaga ggatcactcc cctcttcctg gtgttactct     180
gggtgatatt ggtggaaaat ttggcagtgg tgcatataac agtatggaca atggtgttct     240
gcgatttgac catgtgcgca taccaaggga tcaaatgttg atgaggcttt cacaagttac     300
aagggagggg aaatatgttc attcagatgt cccaaagcag ctgctttatg ggacaatggt     360
ttttgttcgc cagacaatag tcgcagatgc ttctaaggct ttgtcccgtg ctgtttgcat     420
tgctgtacga tacagcgcca tccgaaagca gtttggctct caagatggtg gacctgagac     480
taaggtcctt gattacaaga ctcaacaaag cagactcttt ccgttgctgg cttcagcata     540
tgcatttaga tttgtgggtg actggctgaa gtggctatac atggatgtca ctcagaaact     600
ggaagctaaa gactactcaa cactgcaaga agcccatgcc tgtactgctg gtttgaaggc     660
tgtgacaaca tctgcaacag ctgatgccat tgaagaatgt agaaagctct gtggcggaca     720
tggttacctg aacagcagtg ggcttcctga attgtttgct gtctatgttc ctgcttgcac     780
ttatgaagga gacaatattg ttctgctttt gcaggttgca aggattctaa tgaagaccgt     840
atctcaattg acatctggaa agcaacctgt tggtacaatg gcttacatgg gcaatgtaca     900
atatctgatg caatgcaaat gtgctgttaa cacagccgaa gattggctta accctgttgc     960
```

```
catacaagag gcgtttgaag cccgggctct caggatggca gtaaactgtg cccagaacat    1020
aggccaagca gcaaaccaag aagaaggttt ctatgagcgg tccccctgatt gctagaggc    1080 tgcagtagct cacatccagt tggtcattgt aaccaagttc attgcgaagg tacagcagga    1140
cattcctgga cctggagtga aggaacagct ccagaacctt tgcaatgtct atgccctcta    1200
cattctccac aagcacctgg gcgacttcct ggcaaccggg tgcatcacac ccaagcaggg    1260
agcgctggca aacgagcagc tgggcaagct ttacgcacag gtgcgtccaa atgctgttgc    1320
gctggtggat gccttcaact acacagacca ctacctgggg tctgtgctgg ggcgtacga    1380 tgggaatgtg tacccagcgc tgtacgagga ggcgtggaag gaccctctga acgagacggt    1440
ggtgcccgag gggtaccacg agtacctccg cccccttgctc aagcagcagc tcaagctctc    1500
caggctctag tctgatcggc tacccccct ggaattctcc atggcggctg ccttctcaga    1560
gaatctcacg cgacctccga atgaaagtga tgtaagctac taacgattct tgttagagcc    1620
aggaaagagg ctctccagcc aattataaat ttattcctca agctctgagg atcaagttca    1680
agctgtggat tatataggaa gcacgtttaa taattaataa agagggagag gatgagcatc    1740
tctctgttgc tgctcaaaaa aaaaaaaaa aaaaaaaa aaaaaaaa aaaa             1794
```

<210> SEQ ID NO 4
<211> LENGTH: 502
<212> TYPE: PRT
<213> ORGANISM: Zea mays

<400> SEQUENCE: 4

```
Ser Ala Arg Ala Gln Ser Leu Thr Ser Ser Lys Trp Trp Pro Gly Gly
  1               5                  10                  15

Leu Gly Lys Ala Ser Thr His Ala Val Val Tyr Ala Arg Leu Ile Thr
             20                  25                  30

Glu Gly Lys Asp Tyr Gly Ile His Gly Phe Ile Val Gln Leu Arg Ser
         35                  40                  45

Leu Glu Asp His Ser Pro Leu Pro Gly Val Thr Leu Gly Asp Ile Gly
     50                  55                  60

Gly Lys Phe Gly Ser Gly Ala Tyr Asn Ser Met Asp Asn Gly Val Leu
 65                  70                  75                  80

Arg Phe Asp His Val Arg Ile Pro Arg Asp Gln Met Leu Met Arg Leu
                 85                  90                  95

Ser Gln Val Thr Arg Glu Gly Lys Tyr Val His Ser Asp Val Pro Lys
            100                 105                 110

Gln Leu Leu Tyr Gly Thr Met Val Phe Val Arg Gln Thr Ile Val Ala
        115                 120                 125

Asp Ala Ser Lys Ala Leu Ser Arg Ala Val Cys Ile Ala Val Arg Tyr
    130                 135                 140

Ser Ala Ile Arg Lys Gln Phe Gly Ser Gln Asp Gly Gly Pro Glu Thr
145                 150                 155                 160

Lys Val Leu Asp Tyr Lys Thr Gln Gln Ser Arg Leu Phe Pro Leu Leu
                165                 170                 175

Ala Ser Ala Tyr Ala Phe Arg Phe Val Gly Asp Trp Leu Lys Trp Leu
            180                 185                 190

Tyr Met Asp Val Thr Gln Lys Leu Glu Ala Lys Asp Tyr Ser Thr Leu
        195                 200                 205

Gln Glu Ala His Ala Cys Thr Ala Gly Leu Lys Ala Val Thr Thr Ser
    210                 215                 220
```

```
Ala Thr Ala Asp Ala Ile Glu Glu Cys Arg Lys Leu Cys Gly Gly His
225                 230                 235                 240

Gly Tyr Leu Asn Ser Ser Gly Leu Pro Glu Leu Phe Ala Val Tyr Val
            245                 250                 255

Pro Ala Cys Thr Tyr Glu Gly Asp Asn Ile Val Leu Leu Gln Val
        260                 265                 270

Ala Arg Ile Leu Met Lys Thr Val Ser Gln Leu Thr Ser Gly Lys Gln
        275                 280                 285

Pro Val Gly Thr Met Ala Tyr Met Gly Asn Val Gln Tyr Leu Met Gln
        290                 295                 300

Cys Lys Cys Ala Val Asn Thr Ala Glu Asp Trp Leu Asn Pro Val Ala
305                 310                 315                 320

Ile Gln Glu Ala Phe Glu Ala Arg Ala Leu Arg Met Ala Val Asn Cys
                325                 330                 335

Ala Gln Asn Ile Gly Gln Ala Ala Asn Gln Glu Glu Gly Phe Tyr Glu
            340                 345                 350

Arg Ser Pro Asp Leu Leu Glu Ala Ala Val Ala His Ile Gln Leu Val
            355                 360                 365

Ile Val Thr Lys Phe Ile Ala Lys Val Gln Gln Asp Ile Pro Gly Pro
        370                 375                 380

Gly Val Lys Glu Gln Leu Gln Asn Leu Cys Asn Val Tyr Ala Leu Tyr
385                 390                 395                 400

Ile Leu His Lys His Leu Gly Asp Phe Leu Ala Thr Gly Cys Ile Thr
                405                 410                 415

Pro Lys Gln Gly Ala Leu Ala Asn Glu Gln Leu Gly Lys Leu Tyr Ala
            420                 425                 430

Gln Val Arg Pro Asn Ala Val Ala Leu Val Asp Ala Phe Asn Tyr Thr
            435                 440                 445

Asp His Tyr Leu Gly Ser Val Leu Gly Arg Tyr Asp Gly Asn Val Tyr
        450                 455                 460

Pro Ala Leu Tyr Glu Glu Ala Trp Lys Asp Pro Leu Asn Glu Thr Val
465                 470                 475                 480

Val Pro Glu Gly Tyr His Glu Tyr Leu Arg Pro Leu Leu Lys Gln Gln
                485                 490                 495

Leu Lys Leu Ser Arg Leu
            500

<210> SEQ ID NO 5
<211> LENGTH: 473
<212> TYPE: DNA
<213> ORGANISM: Zea mays
<220> FEATURE:
<221> NAME/KEY: unsure
<222> LOCATION: (8)
<220> FEATURE:
<221> NAME/KEY: unsure
<222> LOCATION: (16)
<220> FEATURE:
<221> NAME/KEY: unsure
<222> LOCATION: (25)
<220> FEATURE:
<221> NAME/KEY: unsure
<222> LOCATION: (40)
<220> FEATURE:
<221> NAME/KEY: unsure
<222> LOCATION: (55)

<400> SEQUENCE: 5
cgcctggnag gatcgnacac tagtngatcc aaataattcn gcacgagtag gaagncacag    60
```

```
cgggaggcca ccatgcggcg gatcgcgtac ctgaatcggc gcggcgtgtt ccgcgggtgg    120
ctcaccgagg acggcgctgc cgccgagctc cgcaaactag cgctcctcga ctgcatcgcc    180
atctatgacc actctctcgc catcaagatt ggcgtccact tcttcctctg ggcagtgcc     240 atcaagtttc ttggaacaaa gcgccaccat gacaagtggt tggttgccac ggaaaattat    300
gatatcaagg gttgttttgc aatgacagaa ctaggccatg aagcaatgt gcgaggaata    360 gaaacaatag caacttatga ttcagaaaca agagagttca tcataaatac tccatgtgaa    420
tcagctcaga agtactggat ttgtggagct gccaatcatg caacacatac aat            473
```

<210> SEQ ID NO 6
<211> LENGTH: 138
<212> TYPE: PRT
<213> ORGANISM: Zea mays
<220> FEATURE:
<221> NAME/KEY: UNSURE
<222> LOCATION: (4)

<400> SEQUENCE: 6

```
Ser Arg Lys Xaa Gln Arg Glu Ala Thr Met Arg Arg Ile Ala Tyr Leu
 1               5                  10                  15

Asn Arg Arg Gly Val Phe Arg Gly Trp Leu Thr Glu Asp Gly Ala Ala
             20                  25                  30

Ala Glu Leu Arg Lys Leu Ala Leu Leu Asp Cys Ile Ala Ile Tyr Asp
         35                  40                  45

His Ser Leu Ala Ile Lys Ile Gly Val His Phe Phe Leu Trp Gly Ser
     50                  55                  60

Ala Ile Lys Phe Leu Gly Thr Lys Arg His His Asp Lys Trp Leu Val
 65                  70                  75                  80

Ala Thr Glu Asn Tyr Asp Ile Lys Gly Cys Phe Ala Met Thr Glu Leu
                 85                  90                  95

Gly His Gly Ser Asn Val Arg Gly Ile Glu Thr Ile Ala Thr Tyr Asp
            100                 105                 110

Ser Glu Thr Arg Glu Phe Ile Ile Asn Thr Pro Cys Glu Ser Ala Gln
        115                 120                 125

Lys Tyr Trp Ile Cys Gly Ala Ala Asn His
    130                 135
```

<210> SEQ ID NO 7
<211> LENGTH: 439
<212> TYPE: DNA
<213> ORGANISM: Zea mays
<220> FEATURE:
<221> NAME/KEY: unsure
<222> LOCATION: (302)
<220> FEATURE:
<221> NAME/KEY: unsure
<222> LOCATION: (306)
<220> FEATURE:
<221> NAME/KEY: unsure
<222> LOCATION: (370)
<220> FEATURE:
<221> NAME/KEY: unsure
<222> LOCATION: (417)..(419)
<220> FEATURE:
<221> NAME/KEY: unsure
<222> LOCATION: (423)

<400> SEQUENCE: 7

```
ccaggctgtt tcgcaatgac agaactacat catggatcga atgtccaagc cctacagact     60
accgctacat tgatcctgt cactgatgag ttcattatta acactccaaa tgatggagct     120
```

| | |
|---|---|
| attaagtggt ggatcggcaa tgctgcgctt catggaaaat ttgctactgt ctttgcaagg | 180 |
| ttaattttac cccttcaagg aaaaggaggg gaggctgctg atatgggcat ccacgcgttt | 240 |
| atcgtcccca tacgggacct tggaaactca cgctgttctt cctgggaatc agatcaatg | 300 |
| antgtngggg cacaagatcg gcctaaaggg tgtagacaat ggtgcgctga ggtttccgct | 360 |
| catttaggan tacccagaga caacttcctt aaacggttcg gtgaagttgt cacgggnnng | 420 |
| ggnaatacac gagcatttg | 439 |

<210> SEQ ID NO 8
<211> LENGTH: 91
<212> TYPE: PRT
<213> ORGANISM: Zea mays

<400> SEQUENCE: 8

```
Pro Gly Cys Phe Ala Met Thr Glu Leu His His Gly Ser Asn Val Gln
 1               5                  10                  15

Ala Leu Gln Thr Thr Ala Thr Phe Asp Pro Val Thr Asp Glu Phe Ile
             20                  25                  30

Ile Asn Thr Pro Asn Asp Gly Ala Ile Lys Trp Trp Ile Gly Asn Ala
         35                  40                  45

Ala Leu His Gly Lys Phe Ala Thr Val Phe Ala Arg Leu Ile Leu Pro
     50                  55                  60

Leu Gln Gly Lys Gly Gly Glu Ala Ala Asp Met Gly Ile His Ala Phe
 65                  70                  75                  80

Ile Val Pro Ile Arg Asp Leu Gly Asn Ser Arg
                 85                  90
```

<210> SEQ ID NO 9
<211> LENGTH: 1609
<212> TYPE: DNA
<213> ORGANISM: Zea mays

<400> SEQUENCE: 9

| | |
|---|---|
| gatagtcttt tgtcaacttc atataaatgg gagaaatgaa ggagttcatg ctttttgtagc | 60 |
| tcaaattagg gatgaagatg gaactgtgtt gcctaatatc catatagctg actgtggcca | 120 |
| taagattgga ctgaatggcg ttgataatgg gcggatttgg tttcaaaata tacgtgttcc | 180 |
| tcgtgagaac ttgcttaatt tggttgctga tgttttgcca gatgggcgat atgttagcat | 240 |
| gatagataat ccagatcaga ggtttgcagc tttcctatct ccgcttacac ttggtcgagt | 300 |
| aaacattgca gttaactcag tctacatttc aaaggtcagc ctagcaattg ctgtgagata | 360 |
| cagtttgtca aggagagcct tttcaattgc accagatgcc cctgaaatgt tgttgcttga | 420 |
| ctatcccagt caccagcgac gccttctacc acttctagca aaagtatgtc tgatgagcag | 480 |
| tgctggcaat tttatgaaaa atatgtatgt aagagaact cctgaaatga gcaaagacat | 540 |
| acacatttac tctagtgctc tgaaggcgac actaacttgg cagaatatga ttacgattca | 600 |
| ggagtgtcgc gaggcctgtg gaggtcaagg tctaaagact gagaaccgca taggaatttt | 660 |
| caaatctgaa tttgatgtcc agtccacatt tgagggtgat aacaatgtgc taatgcagca | 720 |
| ggtaagcaaa gcgctttatg ctgaattttt gggtgcacaa agaagcagc agccattcaa | 780 |
| gggattgggt ttgaacact taaatggctc gagccctgtt attcctgata agctgacaag | 840 |
| tagcatatta aggagctcca gttccagat ggacctgttc tgcttaaggg agagagattt | 900 |
| actgaagcag tttgtagagg aggtttctct ccatcttgca caaggcgaaa gcagagaaaa | 960 |
| ggctttgatg ctgagttatc aagttgctga agacttggct agagcgttta ctgagcgtac | 1020 |

-continued

```
gatcctccaa atattttttgg aggatgagat gaatgttcct tctggttccc taaaggaggt    1080
actgggcttg ctgagatctc tatatgtcat ggtgaacata gatgaatcca catcttttct    1140
aagatacggg catttatcac gtgacaatgt agcccttgtg cggaaagaag tcctgaaact    1200
gtgcagtgaa ctcaggcccc atgcgcttgc tgttgttagt tctttcggaa tccctgatgc    1260
cttccttagt ccacttgctt ttgactggat tgaggcaaat gcactgtcaa ccgggagcca    1320
ctgatctcag gtttccacat acgagccagg ttatcctgtg aaagtactga atattgatgg    1380
cggggcatag ataccgtata actacaggag cacttgttgt ctcggaacaa attgttgtga    1440
atcctgtttt gtataatagt tttcttgaat ataagcgaac gtagcctaac aggccaaagt    1500
ccatgtaatg gggtttacaa cagtaataac ttgcagagtg atgtaagcga gttgttgagc    1560
agtaaataaa atactcttgt cccaaaaaaa aaaaaaaaa aaaaaaaa                   1609
```

<210> SEQ ID NO 10
<211> LENGTH: 451
<212> TYPE: PRT
<213> ORGANISM: Zea mays

<400> SEQUENCE: 10

```
Gly Pro Glu Phe Pro Gly Arg Pro Thr Arg Pro Ile Val Phe Cys Gln
  1               5                  10                  15

Leu His Ile Asn Gly Arg Asn Glu Gly Val His Ala Phe Val Ala Gln
                 20                  25                  30

Ile Arg Asp Glu Asp Gly Thr Val Leu Pro Asn Ile His Ile Ala Asp
             35                  40                  45

Cys Gly His Lys Ile Gly Leu Asn Gly Val Asp Asn Gly Arg Ile Trp
         50                  55                  60

Phe Gln Asn Ile Arg Val Pro Arg Glu Asn Leu Leu Asn Leu Val Ala
 65                  70                  75                  80

Asp Val Leu Pro Asp Gly Arg Tyr Val Ser Met Ile Asp Asn Pro Asp
                 85                  90                  95

Gln Arg Phe Ala Ala Phe Leu Ser Pro Leu Thr Leu Gly Arg Val Asn
                100                 105                 110

Ile Ala Val Asn Ser Val Tyr Ile Ser Lys Val Ser Leu Ala Ile Ala
            115                 120                 125

Val Arg Tyr Ser Leu Ser Arg Arg Ala Phe Ser Ile Ala Pro Asp Ala
        130                 135                 140

Pro Glu Met Leu Leu Leu Asp Tyr Pro Ser His Gln Arg Arg Leu Leu
145                 150                 155                 160

Pro Leu Leu Ala Lys Val Cys Leu Met Ser Ser Ala Gly Asn Phe Met
                165                 170                 175

Lys Asn Met Tyr Val Lys Arg Thr Pro Glu Met Ser Lys Asp Ile His
                180                 185                 190

Ile Tyr Ser Ser Ala Leu Lys Ala Thr Leu Thr Trp Gln Asn Met Ile
            195                 200                 205

Thr Ile Gln Glu Cys Arg Glu Ala Cys Gly Gly Gln Gly Leu Lys Thr
        210                 215                 220

Glu Asn Arg Ile Gly Ile Phe Lys Ser Glu Phe Asp Val Gln Ser Thr
225                 230                 235                 240

Phe Glu Gly Asp Asn Asn Val Leu Met Gln Gln Val Ser Lys Ala Leu
                245                 250                 255

Tyr Ala Glu Phe Leu Gly Ala Gln Lys Lys Gln Gln Pro Phe Lys Gly
                260                 265                 270
```

```
Leu Gly Leu Glu His Leu Asn Gly Ser Ser Pro Val Ile Pro Asp Lys
            275                 280                 285
Leu Thr Ser Ser Ile Leu Arg Ser Ser Lys Phe Gln Met Asp Leu Phe
        290                 295                 300
Cys Leu Arg Glu Arg Asp Leu Leu Lys Gln Phe Val Glu Val Ser
305                 310                 315                 320
Leu His Leu Ala Gln Gly Glu Ser Arg Glu Lys Ala Leu Met Leu Ser
                325                 330                 335
Tyr Gln Val Ala Glu Asp Leu Ala Arg Ala Phe Thr Glu Arg Thr Ile
            340                 345                 350
Leu Gln Ile Phe Leu Glu Asp Glu Met Asn Val Pro Ser Gly Ser Leu
        355                 360                 365
Lys Glu Val Leu Gly Leu Leu Arg Ser Leu Tyr Val Met Val Asn Ile
    370                 375                 380
Asp Glu Ser Thr Ser Phe Leu Arg Tyr Gly His Leu Ser Arg Asp Asn
385                 390                 395                 400
Val Ala Leu Val Arg Lys Glu Val Leu Lys Leu Cys Ser Glu Leu Arg
                405                 410                 415
Pro His Ala Leu Ala Val Val Ser Ser Phe Gly Ile Pro Asp Ala Phe
            420                 425                 430
Leu Ser Pro Leu Ala Phe Asp Trp Ile Glu Ala Asn Ala Leu Ser Thr
        435                 440                 445
Gly Ser His
    450

<210> SEQ ID NO 11
<211> LENGTH: 507
<212> TYPE: DNA
<213> ORGANISM: Argemone mexicana
<220> FEATURE:
<221> NAME/KEY: unsure
<222> LOCATION: (453)

<400> SEQUENCE: 11
gagcaattct ttttgtgtta ttttttgctt tgttgttctt caaaattttc tgattttttt        60
ggttaggtta gattatttgt ttcttcttct cttgaaagac ttgttttaga tagaaaaaat      120
ggaggaagtt gatcacttag ctaatgaaag aaatacagct caatttgatg ttgaatctat      180
gaagattatt tgggctggtt ctcaacatac tttggaagtt tcagagcgga tttctcgtct      240
tgttgctagc gatcctgcct tcgcaaaga caacagagtt atgttaagtc ggaaggatct      300
gtttaaaaac actctgagaa aagcagctca tgcatggaaa cggatcattg agctccgtct      360
ttctgaggaa gaagcgtcct gggttgagat tttatgttga tgaacctgct tttacagatc      420
ttcaatgggg caagtttgga cctgctataa aanggcaagg aactaaagga gcaacaaaga      480
aaagtgggta acaatgggcg tataaga                                           507

<210> SEQ ID NO 12
<211> LENGTH: 121
<212> TYPE: PRT
<213> ORGANISM: Argemone mexicana
<220> FEATURE:
<221> NAME/KEY: UNSURE
<222> LOCATION: (112)

<400> SEQUENCE: 12

Met Glu Glu Val Asp His Leu Ala Asn Glu Arg Asn Thr Ala Gln Phe
1               5                   10                  15
```

```
Asp Val Glu Ser Met Lys Ile Ile Trp Ala Gly Ser Gln His Thr Leu
            20                  25                  30

Glu Val Ser Glu Arg Ile Ser Arg Leu Val Ala Ser Asp Pro Ala Phe
        35                  40                  45

Arg Lys Asp Asn Arg Val Met Leu Ser Arg Lys Asp Leu Phe Lys Asn
    50                  55                  60

Thr Leu Arg Lys Ala Ala His Ala Trp Lys Arg Ile Ile Glu Leu Arg
 65                 70                  75                  80

Leu Ser Glu Glu Ala Ser Trp Leu Arg Phe Tyr Val Asp Glu Pro
                85                  90                  95

Ala Phe Thr Asp Leu Gln Trp Gly Lys Phe Gly Pro Ala Ile Lys Xaa
            100                 105                 110

Gln Gly Thr Lys Gly Ala Thr Lys Lys
        115                 120

<210> SEQ ID NO 13
<211> LENGTH: 410
<212> TYPE: DNA
<213> ORGANISM: Oryza sativa
<220> FEATURE:
<221> NAME/KEY: unsure
<222> LOCATION: (318)

<400> SEQUENCE: 13
cttacaggcg gcgtacctga gggggaggca ccgggacacg caggcgcggg tgttcgagtt      60
cttcctctcg cggcccgacc tccagacgcc cgtcgagatg tccaccgccg cgcaccggga    120
gctctgcttc cggcagctgt gcgcgctggt gcgggaggcc gggtgcgcc cgtcagcct      180 catggcgaac gaccccgccg agtacttcgc cgtcatggag gccgccggcg gcgccgacat    240
ctccctcggc gtcaagctcg gcgtccagta cagcctttgg ggaggttcta taataaatct    300
gggaaccaaa aagcacanag ataggttctt tgacggaatc gacaatttgg attatcctgg    360
ctgttttgct atgacagaag ctgcaccatg gatctaatgt ccaggcccta              410

<210> SEQ ID NO 14
<211> LENGTH: 136
<212> TYPE: PRT
<213> ORGANISM: Oryza sativa
<220> FEATURE:
<221> NAME/KEY: UNSURE
<222> LOCATION: (106)

<400> SEQUENCE: 14

Leu Gln Ala Ala Tyr Leu Arg Gly Arg His Arg Asp Thr Gln Ala Arg
  1               5                  10                  15

Val Phe Glu Phe Phe Leu Ser Arg Pro Asp Leu Gln Thr Pro Val Glu
            20                  25                  30

Met Ser Thr Ala Ala His Arg Glu Leu Cys Phe Arg Gln Leu Cys Ala
        35                  40                  45

Leu Val Arg Glu Ala Gly Val Arg Pro Leu Ser Leu Met Ala Asn Asp
    50                  55                  60

Pro Ala Glu Tyr Phe Ala Val Met Glu Ala Ala Gly Ala Asp Ile
 65                 70                  75                  80

Ser Leu Gly Val Lys Leu Gly Val Gln Tyr Ser Leu Trp Gly Gly Ser
                85                  90                  95

Ile Ile Asn Leu Gly Thr Lys Lys His Xaa Asp Arg Phe Phe Asp Gly
            100                 105                 110
```

```
Ile Asp Asn Leu Asp Tyr Pro Gly Cys Phe Ala Met Thr Glu Leu His
        115                 120                 125

His Gly Ser Asn Val Gln Ala Leu
        130                 135

<210> SEQ ID NO 15
<211> LENGTH: 492
<212> TYPE: DNA
<213> ORGANISM: Oryza sativa
<220> FEATURE:
<221> NAME/KEY: unsure
<222> LOCATION: (353)
<220> FEATURE:
<221> NAME/KEY: unsure
<222> LOCATION: (389)
<220> FEATURE:
<221> NAME/KEY: unsure
<222> LOCATION: (398)
<220> FEATURE:
<221> NAME/KEY: unsure
<222> LOCATION: (425)

<400> SEQUENCE: 15
gtttaaacaa aagtgggga ccctgctgat atgggcattc atgcattcat tgttcccata      60
cgggaccttg acaccaatgc tgttcttccc ggaattgaga tcaatgattg tggtcacaag    120
ataggcctga atggtgtgga caatggtgca ctgaggttcc gttcagtgag gatacctcgt    180
gataatcttc tgaaccgatt cggagacgtg tcacgagatg gaaaatacac aagcagtctg    240
ccaacaatta acaaaagatt tgcagcaacc cttggtgagc ttgttgggg acgcgttggt     300 attgcatata gttctgtagg tatactcaaa gtttcagtga ccattgctgt tangtatgct    360
ctgcttcgac agcaatttgg ccacctaana acctgaantc agtgtgttgg actacaatct    420
cacancataa gctaatgcca tgttgggaac atcataccat tcacttgcca cacggtactt    480 ggggtaatt cc                                                         492

<210> SEQ ID NO 16
<211> LENGTH: 126
<212> TYPE: PRT
<213> ORGANISM: Oryza sativa
<220> FEATURE:
<221> NAME/KEY: UNSURE
<222> LOCATION: (115)

<400> SEQUENCE: 16

Lys Gly Gly Asp Pro Ala Asp Met Gly Ile His Ala Phe Ile Val Pro
  1               5                  10                  15

Ile Arg Asp Leu Asp Thr Asn Ala Val Leu Pro Gly Ile Glu Ile Asn
             20                  25                  30

Asp Cys Gly His Lys Ile Gly Leu Asn Gly Val Asp Asn Gly Ala Leu
         35                  40                  45

Arg Phe Arg Ser Val Arg Ile Pro Arg Asp Asn Leu Leu Asn Arg Phe
     50                  55                  60

Gly Asp Val Ser Arg Asp Gly Lys Tyr Thr Ser Ser Leu Pro Thr Ile
 65                  70                  75                  80

Asn Lys Arg Phe Ala Ala Thr Leu Gly Glu Leu Val Gly Gly Arg Val
                 85                  90                  95

Gly Ile Ala Tyr Ser Ser Val Gly Ile Leu Lys Val Ser Val Thr Ile
            100                 105                 110

Ala Val Xaa Tyr Ala Leu Leu Arg Gln Gln Phe Gly His Leu
        115                 120                 125
```

<210> SEQ ID NO 17
<211> LENGTH: 2323
<212> TYPE: DNA
<213> ORGANISM: Oryza sativa

<400> SEQUENCE: 17

| | | | | | |
|---|---|---|---|---|---|
| gcacgaggtt | ctaacgtggt | gtggacaaga | aaggaaggaa | agatggaggg | cggcgtaggg | 60 |
| ggggaggtgg | accacctcgc | cggcgagagg | gccaccgcgc | agttcgacgt | tgaacacatg | 120 |
| aaggttgcct | gggctggctc | ccgccacgcc | gtcgatgtcg | ccgaccgcat | ggcgcgcctc | 180 |
| gtcgcttccg | accccgtgtt | ccgcaaggat | aacaggacta | tgctccccag | gaaggagctg | 240 |
| ttcaaggaca | cactcagaaa | ggcagcccat | gcgtggaagc | gtatcgtcga | gctccgtctt | 300 |
| acagaagagg | aggcaaattt | gctaaggcta | tacgtggacc | agcctggtta | tgttgatctg | 360 |
| cactgggca | tgtttgttcc | tgctataaaa | ggccaaggga | ctgaagagca | gcagaagaag | 420 |
| tggctacctc | tggcctacag | gttccaaata | attggatgct | atgctcagac | tgaacttggt | 480 |
| catggttcca | atgttcaggg | ccttgaaaca | accgccacat | ttgacccaaa | gactgatgag | 540 |
| tttgttatac | acagcccgac | actgacctct | agcaagtggt | ggcctggtgg | cttgggaaaa | 600 |
| gcttccactc | atgcagttgt | gtatgctcgt | ctgataactg | aaggaaagga | ctacggcata | 660 |
| catggtttca | ttgtgcaact | acgaagccta | gaggaccact | ctcccttcc | cggtgttact | 720 |
| cttggtgata | tcggcggaaa | atttggtagt | ggtgcataca | acagtatgga | taatggagtt | 780 |
| ctgcgatttg | accatgtgcg | catcccaagg | gatcaaatgt | tgatgaggct | ttcacaagtt | 840 |
| acgaaagagg | gaaatatgt | gcactcagat | gtcccaaaac | agctgcttta | tgggacaatg | 900 |
| gtttttgttc | gtcaaacaat | tgttcagat | gcttctaagg | ctttatcacg | tgctacttgc | 960 |
| attgctgtaa | gatacagcgc | tattcgaaag | cagtttggcc | ctcaaactgg | tggccctgag | 1020 |
| actcaggtcc | tcaattacaa | gactcagcaa | agcagactct | tcctttgct | ggcttcagct | 1080 |
| tatgcattta | ggtttgtggg | tgagtggctg | aagtggctgt | acacggatgt | cacacataaa | 1140 |
| ctggaagcca | aggatttctc | aacacttcaa | gaggcccatg | cctgtactgc | tgggttgaag | 1200 |
| gctgtgacaa | catctgcgac | agctgatgga | attgaagaat | gccgaaaact | ctgtggtgga | 1260 |
| catggttacc | tgaacagcag | cgggcttcct | gaattgtttg | ctatctatgt | tcctgcttgc | 1320 |
| acttatgaag | gagacaatgt | tgttttgcta | ttgcaggttg | caaggtttct | aatgaagact | 1380 |
| gtatcccagt | tagcttctgg | aaaacagcct | gttggtacaa | cggcttacat | gggcaacata | 1440 |
| cagtacttga | tgcaatgcaa | atgtggtgta | aatacagctg | aagattggct | aaatcctgct | 1500 |
| gccatacgag | aggtatttga | agctcgggct | ctcaggatgg | cggtgaattg | tgcccagaac | 1560 |
| ataaacaagg | cgccaagcca | agaagaaggg | ttttatgagc | tatcccctga | tctgcttgag | 1620 |
| gtggcggtgg | cccatatcca | gttgataatt | gtaaccaagt | tcatagagaa | attagagcag | 1680 |
| gacatccctg | gtgagggagt | gaaggagcaa | ctgtgcatcc | tttgcaatgt | gtacgcgctg | 1740 |
| tatcttgttc | acaagcatct | gggtgacttc | ctgtcgacgg | ggagcatcac | agcaaggcag | 1800 |
| ggagcgctgg | caaacgagca | gctgggaaag | ctgtatgcgc | aggtgcggcc | gaacgcggtg | 1860 |
| gcgctggtgg | acgcgttcaa | ctacaccgac | cactacctgg | ggtcggtgct | ggggcgctac | 1920 |
| gacggcaatg | tttacccggc | gctgtacgag | gaggcgtgga | aggaccccct | caacgacacg | 1980 |
| gatgtgccgg | acggttacca | ggagcacctc | cgccctctgc | tcaagcagca | gctcaagctc | 2040 |
| tccaggctat | gatcatccat | ccatcatcct | ccctttcttg | ctctatcaat | catatcatac | 2100 |
| tgcatacgat | ttgagtagta | gtaaaataac | accagcatat | gcaaggtgct | ggctggctgc | 2160 |

```
tagtattttc tttttctttta taatttattt atttggggag agctggtatt gtcttattta    2220
tttgggaaga gctggtattg tatgtctggt gatttggtat agctgtaact gtgaacttca    2280
ccacatctcc cccttctcaa gggcatatgc attctactcc tta                      2323

<210> SEQ ID NO 18
<211> LENGTH: 669
<212> TYPE: PRT
<213> ORGANISM: Oryza sativa

<400> SEQUENCE: 18

Met Glu Gly Gly Val Gly Gly Glu Val Asp His Leu Ala Gly Glu Arg
  1               5                  10                  15

Ala Thr Ala Gln Phe Asp Val Glu His Met Lys Val Ala Trp Ala Gly
                 20                  25                  30

Ser Arg His Ala Val Asp Val Ala Asp Arg Met Ala Arg Leu Val Ala
             35                  40                  45

Ser Asp Pro Val Phe Arg Lys Asp Asn Arg Thr Met Leu Pro Arg Lys
         50                  55                  60

Glu Leu Phe Lys Asp Thr Leu Arg Lys Ala Ala His Ala Trp Lys Arg
 65                  70                  75                  80

Ile Val Glu Leu Arg Leu Thr Glu Glu Ala Asn Leu Leu Arg Leu
                 85                  90                  95

Tyr Val Asp Gln Pro Gly Tyr Val Asp Leu His Trp Gly Met Phe Val
                100                 105                 110

Pro Ala Ile Lys Gly Gln Gly Thr Glu Glu Gln Lys Lys Trp Leu
            115                 120                 125

Pro Leu Ala Tyr Arg Phe Gln Ile Ile Gly Cys Tyr Ala Gln Thr Glu
        130                 135                 140

Leu Gly His Gly Ser Asn Val Gln Gly Leu Glu Thr Thr Ala Thr Phe
145                 150                 155                 160

Asp Pro Lys Thr Asp Glu Phe Val Ile His Ser Pro Thr Leu Thr Ser
                165                 170                 175

Ser Lys Trp Trp Pro Gly Gly Leu Gly Lys Ala Ser His Ala Val
            180                 185                 190

Val Tyr Ala Arg Leu Ile Thr Glu Gly Lys Asp Tyr Gly Ile His Gly
        195                 200                 205

Phe Ile Val Gln Leu Arg Ser Leu Glu Asp His Ser Pro Leu Pro Gly
    210                 215                 220

Val Thr Leu Gly Asp Ile Gly Gly Lys Phe Gly Ser Gly Ala Tyr Asn
225                 230                 235                 240

Ser Met Asp Asn Gly Val Leu Arg Phe Asp His Val Arg Ile Pro Arg
                245                 250                 255

Asp Gln Met Leu Met Arg Leu Ser Gln Val Thr Lys Glu Gly Lys Tyr
            260                 265                 270

Val His Ser Asp Val Pro Lys Gln Leu Leu Tyr Gly Thr Met Val Phe
        275                 280                 285

Val Arg Gln Thr Ile Val Ala Asp Ala Ser Lys Ala Leu Ser Arg Ala
    290                 295                 300

Thr Cys Ile Ala Val Arg Tyr Ser Ala Ile Arg Lys Gln Phe Gly Pro
305                 310                 315                 320

Gln Thr Gly Gly Pro Glu Thr Gln Val Leu Asn Tyr Lys Thr Gln Gln
                325                 330                 335

Ser Arg Leu Phe Pro Leu Leu Ala Ser Ala Tyr Ala Phe Arg Phe Val
```

```
                      340            345            350
Gly Glu Trp Leu Lys Trp Leu Tyr Thr Asp Val Thr His Lys Leu Glu
        355                360                365

Ala Lys Asp Phe Ser Thr Leu Gln Glu Ala His Ala Cys Thr Ala Gly
    370                375                380

Leu Lys Ala Val Thr Thr Ser Ala Thr Ala Asp Gly Ile Glu Glu Cys
385                390                395                400

Arg Lys Leu Cys Gly Gly His Gly Tyr Leu Asn Ser Ser Gly Leu Pro
                405                410                415

Glu Leu Phe Ala Ile Tyr Val Pro Ala Cys Thr Tyr Glu Gly Asp Asn
                420                425                430

Val Val Leu Leu Leu Gln Val Ala Arg Phe Leu Met Lys Thr Val Ser
            435                440                445

Gln Leu Ala Ser Gly Lys Gln Pro Val Gly Thr Thr Ala Tyr Met Gly
    450                455                460

Asn Ile Gln Tyr Leu Met Gln Cys Lys Cys Gly Val Asn Thr Ala Glu
465                470                475                480

Asp Trp Leu Asn Pro Ala Ala Ile Arg Glu Val Phe Glu Ala Arg Ala
                485                490                495

Leu Arg Met Ala Val Asn Cys Ala Gln Asn Ile Asn Lys Ala Pro Ser
                500                505                510

Gln Glu Glu Gly Phe Tyr Glu Leu Ser Pro Asp Leu Leu Glu Val Ala
    515                520                525

Val Ala His Ile Gln Leu Ile Ile Val Thr Lys Phe Ile Glu Lys Leu
    530                535                540

Glu Gln Asp Ile Pro Gly Glu Gly Val Lys Glu Gln Leu Cys Ile Leu
545                550                555                560

Cys Asn Val Tyr Ala Leu Tyr Leu Val His Lys His Leu Gly Asp Phe
                565                570                575

Leu Ser Thr Gly Ser Ile Thr Ala Arg Gln Gly Ala Leu Ala Asn Glu
                580                585                590

Gln Leu Gly Lys Leu Tyr Ala Gln Val Arg Pro Asn Ala Val Ala Leu
    595                600                605

Val Asp Ala Phe Asn Tyr Thr Asp His Tyr Leu Gly Ser Val Leu Gly
    610                615                620

Arg Tyr Asp Gly Asn Val Tyr Pro Ala Leu Tyr Glu Glu Ala Trp Lys
625                630                635                640

Asp Pro Leu Asn Asp Thr Asp Val Pro Asp Gly Tyr Gln Glu His Leu
                645                650                655

Arg Pro Leu Leu Lys Gln Gln Leu Lys Leu Ser Arg Leu
                660                665

<210> SEQ ID NO 19
<211> LENGTH: 599
<212> TYPE: DNA
<213> ORGANISM: Glycine max

<400> SEQUENCE: 19
cggtcaactg tacctgctgg ttcattgaag aatgtcttgg gtctattgag atcgttgtat    60
gctgtgatat gtgtggatga agattctgcc tttcttcgat atggatactt gtcaacagag   120
aatgcttctg cagtgaggaa agaagtgcca aaactctgtg ctgaacttcg accacacgca   180
cttgccttgg tcagttcctt tggtattcct gatgcatttt tgagccctat cgcatataat   240
tgggttgatt caaattcttg gtcttctcaa ctttagcaag cttatgcaaa tttctgcata   300
```

```
tgattgagat atgaggttgg cgtgtttgtg gtaagcatat gtgaataatg ttttgttac      360 actatgtaga atattgctga acagtgcaaa taagtttgta ccaatctaat cacgaaataa      420
cgtggttaca tattgtaggg tgaataataa gttaagaaca aaataaaagt tgggctttga      480
cgaaaaatca atgccagatc attcagattg agtttcatca ataaatttct gtaccattta      540
gtaaaaaaaa aaaaaaaaaa aaaaaaaaaa aataactcga gggggggccc gtacacaat       599
```

```
<210> SEQ ID NO 20
<211> LENGTH: 91
<212> TYPE: PRT
<213> ORGANISM: Glycine max

<400> SEQUENCE: 20

Arg Ser Thr Val Pro Ala Gly Ser Leu Lys Asn Val Leu Gly Leu Leu
  1               5                  10                  15

Arg Ser Leu Tyr Ala Val Ile Cys Val Asp Glu Asp Ser Ala Phe Leu
             20                  25                  30

Arg Tyr Gly Tyr Leu Ser Thr Glu Asn Ala Ser Ala Val Arg Lys Glu
         35                  40                  45

Val Pro Lys Leu Cys Ala Glu Leu Arg Pro His Ala Leu Ala Leu Val
     50                  55                  60

Ser Ser Phe Gly Ile Pro Asp Ala Phe Leu Ser Pro Ile Ala Tyr Asn
 65                  70                  75                  80

Trp Val Asp Ser Asn Ser Trp Ser Gln Leu
                 85                  90
```

```
<210> SEQ ID NO 21
<211> LENGTH: 461
<212> TYPE: DNA
<213> ORGANISM: Glycine max
<220> FEATURE:
<221> NAME/KEY: unsure
<222> LOCATION: (185)
<220> FEATURE:
<221> NAME/KEY: unsure
<222> LOCATION: (225)
<220> FEATURE:
<221> NAME/KEY: unsure
<222> LOCATION: (263)
<220> FEATURE:
<221> NAME/KEY: unsure
<222> LOCATION: (374)
<220> FEATURE:
<221> NAME/KEY: unsure
<222> LOCATION: (382)..(383)
<220> FEATURE:
<221> NAME/KEY: unsure
<222> LOCATION: (397)
<220> FEATURE:
<221> NAME/KEY: unsure
<222> LOCATION: (415)
<220> FEATURE:
<221> NAME/KEY: unsure
<222> LOCATION: (436)
<220> FEATURE:
<221> NAME/KEY: unsure
<222> LOCATION: (442)
<220> FEATURE:
<221> NAME/KEY: unsure
<222> LOCATION: (450)
<220> FEATURE:
<221> NAME/KEY: unsure
<222> LOCATION: (453)

<400> SEQUENCE: 21
cacaacacaa tcttcattca tcactgaaac caaagccaca agctgcgaca tcagaaagac      60
```

```
attggcgaga atgaagaca gtattgacca cttggctttc gagaggaaca aggcgcagtt    120
cgatgttgac gagatgaaga tcgtttgggc gggttctcgt caagactttg agctttccga    180
tcggntttct cgccttgttg ccagcgatcc ggccttcaga aaggntgaca gaaccacgct    240
tggtaggaag gagttgttta aanacacctt gagaaaagca gcttatgcat ggtaaaagga    300
tcaacgaagc tccgtcttaa tgaacaggaa gcttataagc tcagattctt tgtggatcaa    360
cctgctttta cggntccttc annggggaa tgtttgngcc ctgctatcca acggncaaag     420
gcactgaccg agccanccag cnagaaagtn ggnttgcctc c                        461
```

<210> SEQ ID NO 22
<211> LENGTH: 129
<212> TYPE: PRT
<213> ORGANISM: Glycine max
<220> FEATURE:
<221> NAME/KEY: UNSURE
<222> LOCATION: (39)
<220> FEATURE:
<221> NAME/KEY: UNSURE
<222> LOCATION: (52)
<220> FEATURE:
<221> NAME/KEY: UNSURE
<222> LOCATION: (65)
<220> FEATURE:
<221> NAME/KEY: UNSURE
<222> LOCATION: (101)
<220> FEATURE:
<221> NAME/KEY: UNSURE
<222> LOCATION: (104)
<220> FEATURE:
<221> NAME/KEY: UNSURE
<222> LOCATION: (109)
<220> FEATURE:
<221> NAME/KEY: UNSURE
<222> LOCATION: (115)
<220> FEATURE:
<221> NAME/KEY: UNSURE
<222> LOCATION: (122)
<220> FEATURE:
<221> NAME/KEY: UNSURE
<222> LOCATION: (124)

<400> SEQUENCE: 22

```
Met Glu Asp Ser Ile Asp His Leu Ala Phe Glu Arg Asn Lys Ala Gln
 1               5                  10                  15

Phe Asp Val Asp Glu Met Lys Ile Val Trp Ala Gly Ser Arg Gln Asp
                20                  25                  30

Phe Glu Leu Ser Asp Arg Xaa Ser Arg Leu Val Ala Ser Asp Pro Ala
            35                  40                  45

Phe Arg Lys Xaa Asp Arg Thr Thr Leu Gly Arg Lys Glu Leu Phe Lys
        50                  55                  60

Xaa Thr Leu Arg Lys Ala Ala Tyr Ala Trp Lys Arg Ile Asn Glu Leu
 65                  70                  75                  80

Arg Leu Asn Glu Gln Glu Ala Tyr Lys Leu Arg Phe Val Asp Gln
                85                  90                  95

Pro Ala Phe Thr Xaa Pro Ser Xaa Gly Glu Cys Leu Xaa Pro Ala Ile
                100                 105                 110

Gln Arg Xaa Lys Ala Leu Thr Glu Pro Xaa Ser Xaa Lys Val Gly Leu
            115                 120                 125

Pro
```

<210> SEQ ID NO 23
<211> LENGTH: 499

```
<212> TYPE: DNA
<213> ORGANISM: Glycine max

<400> SEQUENCE: 23
gcacgagtga tggatttcaa atctatatta ggatatgaaa tcattaaatg aggcatgaga      60
tccactagta tatccaataa atcttggtga atcttagaaa gagagtctca gatagagggg     120
gtggggcagt aaagtttctg ggaaccaagc gccatcatga caagtggttg aattctactg    180
aaaactatga tatcaaggt tgttttgcta tgtcggagtt aggccatgga agtaatgttc     240
gaggaattga aacagtcact acttatgatt caaacaccgg ggaatttgtc atcaatactc    300
catgtgaatc gggtcagaag tattggattg gtggtgcagc aaatcatgca acgcacacta    360
tagtcttttc acagctctat ataaatggaa gcaatcaagg ggtgcatgca tttattgccc    420
aaatcaggga ttcagatggg aacatatgtc caaacatccg aatagctgat tgtggtcaca    480
aaattgggtt taatggagg                                                 499

<210> SEQ ID NO 24
<211> LENGTH: 134
<212> TYPE: PRT
<213> ORGANISM: Glycine max

<400> SEQUENCE: 24

Arg Lys Arg Val Ser Asp Arg Gly Gly Gly Ala Val Lys Phe Leu Gly
  1               5                  10                  15

Thr Lys Arg His His Asp Lys Trp Leu Asn Ser Thr Glu Asn Tyr Asp
             20                  25                  30

Ile Lys Gly Cys Phe Ala Met Ser Glu Leu Gly His Gly Ser Asn Val
         35                  40                  45

Arg Gly Ile Glu Thr Val Thr Thr Tyr Asp Ser Asn Thr Gly Glu Phe
     50                  55                  60

Val Ile Asn Thr Pro Cys Glu Ser Gly Gln Lys Tyr Trp Ile Gly Gly
 65                  70                  75                  80

Ala Ala Asn His Ala Thr His Thr Ile Val Phe Ser Gln Leu Tyr Ile
                 85                  90                  95

Asn Gly Ser Asn Gln Gly Val His Ala Phe Ile Ala Gln Ile Arg Asp
            100                 105                 110

Ser Asp Gly Asn Ile Cys Pro Asn Ile Arg Ile Ala Asp Cys Gly His
        115                 120                 125

Lys Ile Gly Phe Asn Gly
        130

<210> SEQ ID NO 25
<211> LENGTH: 970
<212> TYPE: DNA
<213> ORGANISM: Glycine max
<220> FEATURE:
<221> NAME/KEY: unsure
<222> LOCATION: (295)
<220> FEATURE:
<221> NAME/KEY: unsure
<222> LOCATION: (896)
<220> FEATURE:
<221> NAME/KEY: unsure
<222> LOCATION: (912)

<400> SEQUENCE: 25
accgattcca ccaaacacaa cacagaaaat gcaaacacca aactgcgaag ccgagaggcg      60
aatccagagg ctaaccctac acctaaaccc cacggcgttg gtcgcggcga agcagttgga    120
```

-continued

| | |
|---|---|
| gatggcaacg tgcgctcgcg ggaagctgag cgtggacacg ccgtccttgt ctagttacat | 180 |
| gcgagggaaa cacgtggaca ttcaggagaa ggtgttcgat tacttcaacg cgaacccgcg | 240 |
| ccttcaaact cccgttgaga tctccaagga cgagcatcgc gacctctgca tgaancagtt | 300 |
| aacgggactc gtcagagaag ccgggattcg acccctccgt tacgtagtcg acgatcccgc | 360 |
| taagtacttc gccattttgg aagccgttgg aagcgttgac atgtcgctcg ggatcaagat | 420 |
| ggggtccag tatagtcttt ggggtggttc tgttctcaat ttggggacca agaagcataa | 480 |
| ggataagtac tttgatggga ttgataactt ggactaccct ggttgttttg ctatgaccga | 540 |
| gcttcaccat ggttcaaatg tgcagggcct ccaaactgtt gccacctttg atataatcac | 600 |
| agatgaattt atcattaata caccaaatga tggtgccatc aaatggtgga ttggtaatgc | 660 |
| tgcagtgcac ggcaagtttg ccactgtttt cgctaggttg aaattaccta cttatgacaa | 720 |
| aaaggactt tctgatatgg gtgtccatgc tttcatagtt ccaataaggg atatgaagac | 780 |
| ccatcaacca cttcctggaa ttgagataca tgattgtggt cataaagtcg gcctcaatgg | 840 |
| tgtggataat ggagcatttg agattccgct cggtaagaat tcctcgaaga caatcntcta | 900 |
| aaccgttttg gngatgtctc cccgtgatgg ggaaagtaca cgaagtagcc cttcctacaa | 960 |
| gtaaataagc | 970 |

<210> SEQ ID NO 26
<211> LENGTH: 306
<212> TYPE: PRT
<213> ORGANISM: Glycine max
<220> FEATURE:
<221> NAME/KEY: UNSURE
<222> LOCATION: (98)
<220> FEATURE:
<221> NAME/KEY: UNSURE
<222> LOCATION: (298)

<400> SEQUENCE: 26

```
Pro Ile Pro Pro Asn Thr Thr Gln Lys Met Gln Thr Pro Asn Cys Glu
 1               5                  10                  15

Ala Glu Arg Arg Ile Gln Arg Leu Thr Leu His Leu Asn Pro Thr Ala
            20                  25                  30

Leu Val Ala Ala Lys Gln Leu Glu Met Ala Thr Cys Ala Arg Gly Lys
        35                  40                  45

Leu Ser Val Asp Thr Pro Ser Leu Ser Ser Tyr Met Arg Gly Lys His
    50                  55                  60

Val Asp Ile Gln Glu Lys Val Phe Asp Tyr Phe Asn Ala Asn Pro Arg
65                  70                  75                  80

Leu Gln Thr Pro Val Glu Ile Ser Lys Asp Glu His Arg Asp Leu Cys
                85                  90                  95

Met Xaa Gln Leu Thr Gly Leu Val Arg Glu Ala Gly Ile Arg Pro Leu
            100                 105                 110

Arg Tyr Val Val Asp Asp Pro Ala Lys Tyr Phe Ala Ile Leu Glu Ala
        115                 120                 125

Val Gly Ser Val Asp Met Ser Leu Gly Ile Lys Met Gly Val Gln Tyr
    130                 135                 140

Ser Leu Trp Gly Gly Ser Val Leu Asn Leu Gly Thr Lys Lys His Lys
145                 150                 155                 160

Asp Lys Tyr Phe Asp Gly Ile Asp Asn Leu Asp Tyr Pro Gly Cys Phe
                165                 170                 175

Ala Met Thr Glu Leu His His Gly Ser Asn Val Gln Gly Leu Gln Thr
            180                 185                 190
```

```
Val Ala Thr Phe Asp Ile Ile Thr Asp Glu Phe Ile Asn Thr Pro
        195                 200                 205

Asn Asp Gly Ala Ile Lys Trp Trp Ile Gly Asn Ala Ala Val His Gly
    210                 215                 220

Lys Phe Ala Thr Val Phe Ala Arg Leu Lys Leu Pro Thr Tyr Asp Lys
225                 230                 235                 240

Lys Gly Leu Ser Asp Met Gly Val His Ala Phe Ile Val Pro Ile Arg
                245                 250                 255

Asp Met Lys Thr His Gln Pro Leu Pro Gly Ile Glu Ile His Asp Cys
            260                 265                 270

Gly His Lys Val Gly Leu Asn Gly Val Asp Asn Gly Ala Leu Arg Phe
        275                 280                 285

Arg Ser Val Arg Ile Pro Arg Asp Asn Xaa Leu Asn Arg Phe Gly Asp
    290                 295                 300

Val Ser
305

<210> SEQ ID NO 27
<211> LENGTH: 2379
<212> TYPE: DNA
<213> ORGANISM: Triticum aestivum

<400> SEQUENCE: 27
gcacgagggc gagttggagc aggtctgggt ctggccgcgt gagttatttc ccagccaggc      60
atctgagagc tttggtcttg acctcgacag agatcgccat ggacgcatcg gcggaggtgg     120
accacctcgc cgccgagagg tcggccgcgc gcttcgacgt cgaggcgatg aaggttgcat     180
gggctggctc gcgacacgcc gtcgaagtcg gcgaccgcat ggcccgactc gtcgcgtccg     240
accctgtctt ccgcaaggat aacaggacca tgctctccag gaaggacttg tttaaggaca     300
ctctaagaaa ggcagcccat gcatggaagc gtattgtcga actacgtctc acagaggagg     360
aagcaggtat gctgaggcta tatgtcgatc agcctggtta tgttgatctg cattggggca     420
tgtttgttcc tgctataaaa ggtcaaggta ctgaggagca gcagaaaaag tggttaccaa     480
tggcttacaa gttccaaata attgggtgct atgctcagac tgaactcggt catggctcaa     540
acgttcaggg ccttgaaaca actgccacat tgatccaaa gactgatgag tttgtcatcc      600
acagtccaac tctgacctcc agcaaatggt ggcctggtgg cttggggaaa gcttccactc     660
atgcagtggt gtatgctcgg ctgataactg aaggaaagga ctatggtata catggtttca     720
ttgtgcaact gcgaagctta gaggatcact cccctcttcc tggtgttact ctgggtgata     780
ttggtggaaa atttggcagt ggtgcatata acagtatgga caatggtgtt ctgcgatttg     840
accatgtgcg cataccaagg gatcaaatgt tgatgaggct ttcacaagtt acaagggagg     900
ggaaatatgt tcattcagat gtcccaaagc agctgcttta tgggacaatg gttttgttc      960 gccagacaat agtcgcagat gcttctaagg cttgtcccg tgctgtttgc attgctgtac    1020
gatacagcgc catccgaaag cagttttggct ctcaagatgg tggacctgag actaaggtcc    1080
ttgattacaa gactcaacaa agcagactct tccgttgct ggcttcagca tatgcattta    1140
gatttgtggg tgactggctg aagtggctat acatggatgt cactcagaaa ctggaagcta    1200
aagactactc aacactgcaa gaagcccatg cctgtactgc tggtttgaag gctgtgacaa    1260
catctgcaac agctgatgcc attgaagaat gtagaaagct ctgtggcgga catggttacc    1320
tgaacagcag tgggcttcct gaattgtttg ctgtctatgt tcctgcttgc acttatgaag    1380
```

-continued

```
gagacaatat tgttctgctt ttgcaggttg caaggattct aatgaagacc gtatctcaat      1440
tgacatctgg aaagcaacct gttggtacaa tggcttacat gggcaatgta caatatctga      1500
tgcaatgcaa atgtgctgtt aacacagccg aagattggct taaccctgtt gccatacaag      1560
aggcgtttga agcccgggct ctcaggatgg cagtaaactg tgcccagaac ataggccaag      1620
cagcaaacca agaagaaggt ttctatgagc ggtcccctga tttgctagag gctgcagtag      1680
ctcacatcca gttggtcatt gtaaccaagt tcattgcgaa ggtacagcag acattcctg       1740 gacctggagt gaaggaacag ctccagaacc tttgcaatgt ctatgccctc tacattctcc      1800
acaagcacct gggcgacttc ctggcaaccg ggtgcatcac acccaagcag ggagcgctgg      1860
caaacgagca gctgggcaag ctttacgcac aggtgcgtcc aaatgctgtt gcgctggtgg      1920
atgccttcaa ctacacagac cactacctgg ggtctgtgct ggggcggtac gatgggaatg      1980
tgtacccagc gctgtacgag gaggcgtgga aggaccctct gaacgagacg gtggtgcccg      2040
aggggtacca cgagtacctc cgccccttgc tcaagcagca gctcaagctc tccaggctct      2100
agtctgatcg ctacccccc ctggaattct ccatggcggc tgccttctca gagaatctca       2160
cgcgacctcc gaatgaaagt gatgtaagct actaacgatt cttgttagag ccaggaaaga      2220
ggctctccag ccaattataa atttattcct caagctctga ggatcaagtt caagctgtgg      2280
attatatagg aagcacgttt aataattaat aaagagggag aggatgagca tctctctgtt      2340
gctgctcaaa aaaaaaaaa aaaaaaaaaa aaaaaaaa                              2379
```

<210> SEQ ID NO 28
<211> LENGTH: 667
<212> TYPE: PRT
<213> ORGANISM: Triticum aestivum

<400> SEQUENCE: 28

```
Met Asp Ala Ser Ala Glu Val Asp His Leu Ala Ala Glu Arg Ser Ala
 1               5                  10                  15

Ala Arg Phe Asp Val Glu Ala Met Lys Val Ala Trp Ala Gly Ser Arg
            20                  25                  30

His Ala Val Glu Val Gly Asp Arg Met Ala Arg Leu Val Ala Ser Asp
        35                  40                  45

Pro Val Phe Arg Lys Asp Asn Arg Thr Met Leu Ser Arg Lys Asp Leu
    50                  55                  60

Phe Lys Asp Thr Leu Arg Lys Ala Ala His Ala Trp Lys Arg Ile Val
65                  70                  75                  80

Glu Leu Arg Leu Thr Glu Glu Ala Gly Met Leu Arg Leu Tyr Val
                85                  90                  95

Asp Gln Pro Gly Tyr Val Asp Leu His Trp Gly Met Phe Val Pro Ala
            100                 105                 110

Ile Lys Gly Gln Gly Thr Glu Gly Gln Gln Lys Lys Trp Leu Pro Met
        115                 120                 125

Ala Tyr Lys Phe Gln Ile Ile Gly Cys Tyr Ala Gln Thr Glu Leu Gly
    130                 135                 140

His Gly Ser Asn Val Gln Gly Leu Glu Thr Thr Ala Thr Phe Asp Pro
145                 150                 155                 160

Lys Thr Asp Glu Phe Val Ile His Ser Pro Thr Leu Thr Ser Ser Lys
                165                 170                 175

Trp Trp Pro Gly Gly Leu Gly Lys Ala Ser Thr His Ala Val Val Tyr
            180                 185                 190

Ala Arg Leu Ile Thr Glu Gly Lys Asp Tyr Gly Ile His Gly Phe Ile
```

```
            195                 200                 205
Val Gln Leu Arg Ser Leu Glu Asp His Ser Pro Leu Pro Gly Val Thr
    210                 215                 220

Leu Gly Asp Ile Gly Gly Lys Phe Gly Ser Gly Ala Tyr Asn Ser Met
225                 230                 235                 240

Asp Asn Gly Val Leu Arg Phe Asp His Val Arg Ile Pro Arg Asp Gln
                245                 250                 255

Met Leu Met Arg Leu Ser Gln Val Thr Arg Glu Gly Lys Tyr Val His
            260                 265                 270

Ser Asp Val Pro Lys Gln Leu Leu Tyr Gly Thr Met Val Phe Val Arg
        275                 280                 285

Gln Thr Ile Val Ala Asp Ala Ser Lys Ala Leu Ser Arg Ala Val Cys
    290                 295                 300

Ile Ala Val Arg Tyr Ser Ala Ile Arg Lys Gln Phe Gly Ser Gln Asp
305                 310                 315                 320

Gly Gly Pro Glu Thr Lys Val Leu Asp Tyr Lys Thr Gln Gln Ser Arg
                325                 330                 335

Leu Phe Pro Leu Leu Ala Ser Ala Tyr Ala Phe Arg Phe Val Gly Asp
            340                 345                 350

Trp Leu Lys Trp Leu Tyr Met Asp Val Thr Gln Lys Leu Glu Ala Lys
        355                 360                 365

Asp Tyr Ser Thr Leu Gln Glu Ala His Ala Cys Thr Ala Gly Leu Lys
    370                 375                 380

Ala Val Thr Thr Ser Ala Thr Ala Asp Ala Ile Glu Glu Cys Arg Lys
385                 390                 395                 400

Leu Cys Gly Gly His Gly Tyr Leu Asn Ser Ser Gly Leu Pro Glu Leu
                405                 410                 415

Phe Ala Val Tyr Val Pro Ala Cys Thr Tyr Glu Gly Asp Asn Ile Val
            420                 425                 430

Leu Leu Leu Gln Val Ala Arg Ile Leu Met Lys Thr Val Ser Gln Leu
        435                 440                 445

Thr Ser Gly Lys Gln Pro Val Gly Thr Met Ala Tyr Met Gly Asn Val
    450                 455                 460

Gln Tyr Leu Met Gln Cys Lys Cys Ala Val Asn Thr Ala Glu Asp Trp
465                 470                 475                 480

Leu Asn Pro Val Ala Ile Gln Glu Ala Phe Glu Ala Arg Ala Leu Arg
                485                 490                 495

Met Ala Val Asn Cys Ala Gln Asn Ile Gly Gln Ala Ala Asn Gln Glu
            500                 505                 510

Glu Gly Phe Tyr Glu Arg Ser Pro Asp Leu Leu Glu Ala Ala Val Ala
        515                 520                 525

His Ile Gln Leu Val Ile Val Thr Lys Phe Ile Ala Lys Val Gln Gln
    530                 535                 540

Asp Ile Pro Gly Pro Gly Val Lys Glu Gln Leu Gln Asn Leu Cys Asn
545                 550                 555                 560

Val Tyr Ala Leu Tyr Ile Leu His Lys His Leu Gly Asp Phe Leu Ala
                565                 570                 575

Thr Gly Cys Ile Thr Pro Lys Gln Gly Ala Leu Ala Asn Glu Gln Leu
            580                 585                 590

Gly Lys Leu Tyr Ala Gln Val Arg Pro Asn Ala Val Ala Leu Val Asp
        595                 600                 605

Ala Phe Asn Tyr Thr Asp His Tyr Leu Gly Ser Val Leu Gly Arg Tyr
    610                 615                 620
```

```
Asp Gly Asn Val Tyr Pro Ala Leu Tyr Glu Ala Trp Lys Asp Pro
625                 630                 635                 640

Leu Asn Glu Thr Val Val Pro Glu Gly Tyr His Glu Tyr Leu Arg Pro
            645                 650                 655

Leu Leu Lys Gln Gln Leu Lys Leu Ser Arg Leu
        660                 665

<210> SEQ ID NO 29
<211> LENGTH: 313
<212> TYPE: PRT
<213> ORGANISM: Arabidopsis thaliana

<400> SEQUENCE: 29

Met Glu Ser Arg Arg Glu Lys Asn Pro Met Thr Glu Glu Ser Asp
 1               5                  10                  15

Gly Leu Ile Ala Ala Arg Arg Ile Gln Arg Leu Ser Leu His Leu Ser
            20                  25                  30

Pro Ser Leu Thr Leu Ser Pro Ser Leu Pro Leu Val Gln Thr Glu Thr
                35                  40                  45

Cys Ser Ala Arg Ser Lys Lys Leu Asp Val Asn Gly Glu Ala Leu Ser
        50                  55                  60

Leu Tyr Met Arg Gly Lys His Ile Asp Ile Gln Glu Lys Ile Phe Asp
65                  70                  75                  80

Phe Phe Asn Ser Arg Pro Asp Leu Gln Thr Pro Ile Glu Ile Ser Lys
                85                  90                  95

Asp Asp His Arg Glu Leu Cys Met Asn Gln Leu Ile Gly Leu Val Arg
            100                 105                 110

Glu Ala Gly Val Arg Pro Phe Arg Tyr Val Ala Asp Asp Pro Glu Lys
        115                 120                 125

Tyr Phe Ala Ile Met Glu Ala Val Gly Ser Val Asp Met Ser Leu Gly
    130                 135                 140

Ile Lys Met Gly Val Gln Tyr Ser Leu Trp Gly Gly Ser Val Ile Asn
145                 150                 155                 160

Leu Gly Thr Lys Lys His Arg Asp Lys Tyr Phe Asp Gly Ile Asp Asn
                165                 170                 175

Leu Asp Tyr Thr Gly Cys Phe Ala Met Thr Glu Leu His His Gly Ser
            180                 185                 190

Asn Val Gln Gly Leu Gln Thr Thr Ala Thr Phe Asp Pro Leu Lys Asp
        195                 200                 205

Glu Phe Val Ile Asp Thr Pro Asn Asp Gly Ala Ile Lys Trp Trp Ile
    210                 215                 220

Gly Asn Ala Ala Val His Gly Lys Phe Ala Thr Val Phe Ala Arg Leu
225                 230                 235                 240

Ile Leu Pro Thr His Asp Ser Lys Gly Val Ser Asp Met Gly Val His
                245                 250                 255

Ala Phe Ile Val Pro Ile Arg Asp Met Lys Thr His Gln Thr Leu Pro
            260                 265                 270

Gly Val Glu Ile Gln Asp Cys Gly His Lys Val Gly Leu Asn Gly Val
        275                 280                 285

Asp Asn Gly Ala Leu Arg Phe Ser Val Arg Ile Pro Arg Asp Asn
    290                 295                 300

Leu Leu Asn Arg Phe Gly Asp Val Ser
305                 310
```

```
<210> SEQ ID NO 30
<211> LENGTH: 664
<212> TYPE: PRT
<213> ORGANISM: Arabidopsis thaliana

<400> SEQUENCE: 30

Met Glu Gly Ile Asp His Leu Ala Asp Glu Arg Asn Lys Ala Glu Phe
  1               5                  10                  15

Asp Val Glu Asp Met Lys Ile Val Trp Ala Gly Ser Arg His Ala Phe
             20                  25                  30

Glu Val Ser Asp Arg Ile Ala Arg Leu Val Ala Ser Asp Pro Val Phe
         35                  40                  45

Glu Lys Ser Asn Arg Ala Arg Leu Ser Arg Lys Glu Leu Phe Lys Ser
     50                  55                  60

Thr Leu Arg Lys Cys Ala His Ala Phe Lys Arg Ile Ile Glu Leu Arg
 65                  70                  75                  80

Leu Asn Glu Glu Glu Ala Gly Arg Leu Arg His Phe Ile Asp Gln Pro
                 85                  90                  95

Ala Tyr Val Asp Leu His Trp Gly Met Phe Val Pro Ala Ile Lys Gly
            100                 105                 110

Gln Gly Thr Glu Glu Gln Gln Lys Lys Trp Leu Ser Leu Ala Asn Lys
        115                 120                 125

Met Gln Ile Ile Gly Cys Tyr Ala Gln Thr Glu Leu Gly His Gly Ser
    130                 135                 140

Asn Val Gln Gly Leu Glu Thr Thr Ala Thr Phe Asp Pro Lys Thr Asp
145                 150                 155                 160

Glu Phe Val Ile His Thr Pro Thr Gln Thr Ala Ser Lys Trp Trp Pro
                165                 170                 175

Gly Gly Leu Gly Lys Val Ser Thr His Ala Val Val Tyr Ala Arg Leu
            180                 185                 190

Ile Thr Asn Gly Lys Asp Tyr Gly Ile His Gly Phe Ile Val Gln Leu
        195                 200                 205

Arg Ser Leu Glu Asp His Ser Pro Leu Pro Asn Ile Thr Val Gly Asp
    210                 215                 220

Ile Gly Thr Lys Met Gly Asn Gly Ala Tyr Asn Ser Met Asp Asn Gly
225                 230                 235                 240

Phe Leu Met Phe Asp His Val Arg Ile Pro Arg Asp Gln Met Leu Met
                245                 250                 255

Arg Leu Ser Lys Val Thr Arg Glu Gly Glu Tyr Val Pro Ser Asp Val
            260                 265                 270

Pro Lys Gln Leu Val Tyr Gly Thr Met Val Tyr Val Arg Gln Thr Ile
        275                 280                 285

Val Ala Asp Ala Ser Asn Ala Leu Ser Arg Ala Val Cys Ile Ala Thr
    290                 295                 300

Arg Tyr Ser Ala Val Arg Arg Gln Phe Gly Ala His Asn Gly Gly Ile
305                 310                 315                 320

Glu Thr Gln Val Ile Asp Tyr Lys Thr Gln Gln Asn Arg Leu Phe Pro
                325                 330                 335

Leu Leu Ala Ser Ala Tyr Ala Phe Arg Phe Val Gly Glu Trp Leu Lys
            340                 345                 350

Trp Leu Tyr Thr Asp Val Thr Glu Arg Leu Ala Ala Ser Asp Phe Ala
        355                 360                 365

Thr Leu Pro Glu Ala His Ala Cys Thr Ala Gly Leu Lys Ser Leu Thr
    370                 375                 380
```

```
Thr Thr Ala Thr Ala Asp Gly Ile Glu Glu Cys Arg Lys Leu Cys Gly
385                 390                 395                 400

Gly His Gly Tyr Leu Trp Cys Ser Gly Leu Pro Glu Leu Phe Ala Val
                405                 410                 415

Tyr Val Pro Ala Cys Thr Tyr Glu Gly Asp Asn Val Val Leu Gln Leu
                420                 425                 430

Gln Val Ala Arg Phe Leu Met Lys Thr Val Ala Gln Leu Gly Ser Gly
                435                 440                 445

Lys Val Pro Val Gly Thr Thr Ala Tyr Met Gly Arg Ala Ala His Leu
450                 455                 460

Leu Gln Cys Arg Ser Gly Val Gln Lys Ala Glu Asp Trp Leu Asn Pro
465                 470                 475                 480

Asp Val Val Leu Glu Ala Phe Glu Ala Arg Ala Leu Arg Met Ala Val
                485                 490                 495

Thr Cys Ala Lys Asn Leu Ser Lys Phe Glu Asn Gln Glu Gln Gly Phe
                500                 505                 510

Gln Glu Leu Leu Ala Asp Leu Val Glu Ala Ala Ile Ala His Cys Gln
                515                 520                 525

Leu Ile Val Val Ser Lys Phe Ile Ala Lys Leu Glu Gln Asp Ile Gly
530                 535                 540

Gly Lys Gly Val Lys Lys Gln Leu Asn Asn Leu Cys Tyr Ile Tyr Ala
545                 550                 555                 560

Leu Tyr Leu Leu His Lys His Leu Gly Asp Phe Leu Ser Thr Asn Cys
                565                 570                 575

Ile Thr Pro Lys Gln Ala Ser Leu Ala Asn Asp Gln Leu Arg Ser Leu
                580                 585                 590

Tyr Thr Gln Val Arg Pro Asn Ala Val Ala Leu Val Asp Ala Phe Asn
                595                 600                 605

Tyr Thr Asp His Tyr Leu Asn Ser Val Leu Gly Arg Tyr Asp Gly Asn
                610                 615                 620

Val Tyr Pro Lys Leu Phe Glu Glu Ala Leu Lys Asp Pro Leu Asn Asp
625                 630                 635                 640

Ser Val Val Pro Asp Gly Tyr Gln Glu Tyr Leu Arg Pro Val Leu Gln
                645                 650                 655

Gln Gln Leu Arg Thr Ala Arg Leu
                660

<210> SEQ ID NO 31
<211> LENGTH: 433
<212> TYPE: PRT
<213> ORGANISM: Myxococcus xanthus

<400> SEQUENCE: 31

Leu Glu Val Gly Gly Arg Val Leu Gly Val His Ala Leu Leu Val Pro
1               5                   10                  15

Leu Arg Asp Pro Ala Gly Lys Val Leu Pro Gly Ile Arg Ile Glu Asp
                20                  25                  30

Cys Gly Glu Lys Met Gly Leu Asn Gly Val Asp Asn Gly Arg Ile Trp
            35                  40                  45

Phe Glu His Val Arg Val Pro Arg Glu Asn Leu Leu Asp Arg Phe Gly
        50                  55                  60

Gln Val Asn Ala Gln Gly Glu Tyr Thr Ser Ala Ile Thr Gly Asp Ser
65                  70                  75                  80

Lys Arg Phe Phe Thr Met Leu Gly Thr Leu Val Ala Gly Arg Val Ser
                85                  90                  95
```

-continued

```
Val Ala Ala Ala Ala Leu Ser Ala Lys Ser Gly Leu Thr Ile Ala
            100                 105                 110

Val Arg Tyr Gly Asp Leu Arg Arg Gln Phe Gly Pro Ala Gly Asp Lys
            115                 120                 125

Glu Phe Arg Leu Leu Asp His Gln Ala His Gln Arg Arg Leu Leu Val
    130                 135                 140

Pro Leu Ala Lys Thr Tyr Ala Met Asp Phe Ala Leu Glu Tyr Leu Val
145                 150                 155                 160

Glu Arg Tyr Val Lys Arg Thr Glu Glu Asp Ala Arg Glu Val Glu Ser
                165                 170                 175

Leu Ala Ala Gly Leu Lys Ala Tyr Ser Thr Trp His Thr Thr Ala Val
                180                 185                 190

Leu Gln Glu Ala Arg Glu Ala Cys Gly Gly Gln Gly Tyr Leu Gln Ala
        195                 200                 205

Asn Arg Leu Ala Ala Leu Lys Ala Asp Thr Asp Val Phe Thr Thr Phe
    210                 215                 220

Glu Gly Asp Asn Thr Val Leu Met Gln Leu Val Ala Lys Gly Leu Leu
225                 230                 235                 240

Thr Gly Tyr Arg Gln Arg Phe Glu Asp Arg Val Phe Ala Val Leu
                245                 250                 255

Lys Leu Leu Ala Asp Arg Ala Thr Ala Val Val Asp Arg Asn Pro Phe
                260                 265                 270

Ala Ala Arg Arg Thr Asp Ser Asp His Leu Arg Asp Asn Asp Tyr His
            275                 280                 285

Leu Arg Ala Leu Arg Phe Arg Glu Glu Glu Leu Leu Ala Thr Val Ser
    290                 295                 300

Gln Arg Ile Arg Lys Arg Leu Ser Ala Gly Val Glu Ala Phe Glu Ala
305                 310                 315                 320

Phe Asn Gln Val Gln Val His Leu Leu Glu Leu Ala His Ala His Val
                325                 330                 335

Glu Arg Leu Val Leu Glu Gln Phe Leu Lys Gly Val Ala Asp Val Lys
                340                 345                 350

Asp Pro Gly Leu Lys Thr Val Leu Gly Arg Leu Cys Asp Leu Tyr Gly
            355                 360                 365

Leu Ser Cys Leu Glu Ser Ala Asn Gly Trp Phe Gln Glu His Gly Trp
    370                 375                 380

Leu Glu Gly Thr Lys Val Lys Ala Ile Arg Lys Glu Val Thr Arg Leu
385                 390                 395                 400

Cys Ala Glu Leu Arg Pro Asp Ala Val Ala Leu Val Asn Ala Phe Gly
                405                 410                 415

Val Pro Asp Thr Cys Leu Ala Ala Pro Ile Gly Leu Gly His Leu Ser
            420                 425                 430

Pro
```